(12) United States Patent
Robinson

(10) Patent No.: US 9,863,701 B2
(45) Date of Patent: Jan. 9, 2018

(54) COMPOSITIONS AND METHODS FOR ATMOSPHERIC SPRAY FREEZE DRYING

(71) Applicant: Aerosol Therapeutics, LLC, New York, NY (US)

(72) Inventor: Thomas D. Robinson, New York, NY (US)

(73) Assignee: Aerosol Therapeutics, LLC, New York, NY (US)

( * ) Notice: Subject to any disclaimer, the term of this patent is extended or adjusted under 35 U.S.C. 154(b) by 0 days.

(21) Appl. No.: 15/248,932

(22) Filed: Aug. 26, 2016

(65) Prior Publication Data

US 2017/0082362 A1  Mar. 23, 2017

Related U.S. Application Data

(63) Continuation of application No. 14/577,436, filed on Dec. 19, 2014, now Pat. No. 9,453,676.

(60) Provisional application No. 61/918,414, filed on Dec. 19, 2013.

(51) Int. Cl.

| F26B 5/06 | (2006.01) |
|---|---|
| C08L 5/00 | (2006.01) |
| C08L 5/02 | (2006.01) |
| C08B 37/02 | (2006.01) |
| A61K 9/19 | (2006.01) |
| A61K 9/16 | (2006.01) |

(52) U.S. Cl.
CPC ............ *F26B 5/065* (2013.01); *A61K 9/1688* (2013.01); *A61K 9/19* (2013.01); *C08B 37/0021* (2013.01); *C08L 5/00* (2013.01); *C08L 5/02* (2013.01); *A61K 9/1623* (2013.01); *A61K 9/1652* (2013.01); *A61K 9/1658* (2013.01)

(58) Field of Classification Search
CPC ......... F26B 5/065; A61K 9/1688; A61K 9/19; A61K 9/1623; A61K 9/1652; A61K 9/1658; C08B 37/0021; C08B 5/00; C08B 5/02
USPC ............................................. 34/92, 278, 286
See application file for complete search history.

(56) References Cited

U.S. PATENT DOCUMENTS

| 6,344,182 B1 * | 2/2002 | Sutton ................. A61K 9/1658 424/489 |
|---|---|---|
| 6,468,551 B1 * | 10/2002 | Diec ..................... A61K 8/042 424/401 |
| 7,007,406 B2 | 3/2006 | Wang et al. |
| 7,073,349 B2 * | 7/2006 | Shekunov ............ A61K 9/1623 210/808 |

(Continued)

FOREIGN PATENT DOCUMENTS

| CA | 2934066 A1 * | 6/2015 | .............. F26B 5/065 |
|---|---|---|---|
| EP | 1590613 B1 * | 4/2014 | ........... A61K 9/1623 |

(Continued)

OTHER PUBLICATIONS

PCT/US2014/071545 International Search Report and Written Opinion, dated Mar. 12, 2015, 14 pages.

(Continued)

*Primary Examiner* — Stephen M Gravini
(74) *Attorney, Agent, or Firm* — Dennis A. Bennett; Clifford A. Schlecht

(57) ABSTRACT

Methods of preparing dried powders of biologically active compositions are disclosed. They are designed to provide dried material that maintains biological activity at low economic cost. Compositions made by the above methods are also described.

22 Claims, 15 Drawing Sheets

(56) References Cited

U.S. PATENT DOCUMENTS

| | | | |
|---|---|---|---|
| 7,229,645 B2 * | 6/2007 | Maa | A61K 9/0021 424/184.1 |
| 7,363,726 B2 | 4/2008 | Wang et al. | |
| 7,806,206 B1 | 10/2010 | Miess | |
| 7,842,310 B2 | 11/2010 | Hwang et al. | |
| 7,923,029 B2 * | 4/2011 | Truong-Le | A01N 1/02 424/489 |
| 7,972,622 B1 * | 7/2011 | Coffee | A61J 3/00 424/434 |
| 8,322,046 B2 * | 12/2012 | Wang | A61K 9/1623 134/172 |
| 8,337,895 B2 | 12/2012 | Bennett et al. | |
| 8,533,972 B2 | 9/2013 | Hubbard, Jr. et al. | |
| 8,689,459 B2 | 4/2014 | Poortinga et al. | |
| 8,769,841 B2 | 7/2014 | Gruber et al. | |
| 9,052,138 B2 * | 6/2015 | DeMarco | F26B 5/065 |
| 9,453,676 B2 * | 9/2016 | Robinson | F26B 5/065 |
| 2004/0154317 A1 * | 8/2004 | Shekunov | A61K 9/1623 62/64 |
| 2005/0178020 A1 | 8/2005 | Shekunov et al. | |
| 2007/0190158 A1 | 8/2007 | Hwang et al. | |
| 2010/0297214 A1 * | 11/2010 | Haas | A61K 9/1682 424/450 |
| 2015/0175716 A1 | 6/2015 | Robinson | |

FOREIGN PATENT DOCUMENTS

| | | | |
|---|---|---|---|
| EP | 3082771 A1 * | 10/2016 | F26B 5/065 |
| WO | WO 2015/095730 | * 6/2015 | |
| WO | WO 2015095730 A1 | 6/2015 | |

OTHER PUBLICATIONS

PCT/US2014/071545 International Preliminary Report on Patentability, dated Jun. 21, 2016, 7 pages.

Leuenberger, Hans, et al., "Spray Freeze Drying in a Fluidized Bed at Normail and Low Pressure", Drying Technology, 2006, 24: 711-719.

Wang, Z.L., et al., "Powder formation by atmospheric spray-freeze-drying", Powder Technology, Nov. 2006, 170: 45-52.

* cited by examiner

COMPOSITIONS AND METHODS FOR ATMOSPHERIC SPRAY FREEZE DRYING

CROSS-REFERENCE TO RELATED APPLICATIONS

This application is a continuation of U.S. application Ser. No. 14/577,436, filed Dec. 19, 2014, which claims the benefit of U.S. Provisional Patent Application No. 61/918,414 filed on Dec. 19, 2013, which is hereby incorporated by reference in their entirety to the extent not inconsistent with the present description.

BACKGROUND

Field

The present disclosure relates to compositions and methods for preparing dried powders, more specifically to methods for preparing dried powders of pharmacologically active compositions.

Related Art

Proteins, hormones, antibodies, vaccines, blood plasma, and other fragile molecules stored as aqueous solutions have short shelf lives. They must be refrigerated (typically maintained in an environment of 2 to 8° C.). Even under the best of circumstances, many solution-based formulations exhibit a protein concentration loss over time, which is presumably due to the formation of dimers and other protein aggregates in solution. Such formulations frequently must be supplemented with stabilizing additives such as buffers and/or antioxidants to minimize solution instability.

By removing the water from the material, such products may be easily stored for longer durations. Once dried, such material can be shipped and later reconstituted to its original active form for injection. Since many of these materials are heat-sensitive and require special care during the drying process, formulations of these materials frequently must be supplemented with stabilizing additives such as buffers and/or antioxidants to minimize solution instability in addition to other excipients.

Lyophilization is often used to dry these fragile substances. Lyophilization works by freezing the material and then reducing the surrounding vapor pressure to allow the frozen water in the material to sublimate directly from the solid phase to the gas phase. A very low operating temperature avoids damaging these heat-sensitive products; however, it is a slow expensive process, requiring costly equipment and considerable energy. In addition, solutions of such products must be supplemented with cryoprotectants to minimize the damage caused by freezing. Such formulation development is time consuming and expensive.

Lyophilized powders are typically formed as cakes; in many cases requiring additional grinding and milling and optionally sieving processing in order to create flowing powders. In the past few years, spray drying has been employed as an alternative approach for preparing a number of therapeutic protein-based powders. Unfortunately, certain proteins, hormones, antibodies, and cytokines in particular, are prone to degradation during spray drying, and loss of their secondary structure, due to heat.

Thus, there remains a need for an improved method for preparing dried powders of biologically active compositions, which provides dried material that maintains its biological activity for a long time at low economic cost.

SUMMARY

Accordingly, the inventor herein discloses new compositions and methods for preparing dried powders at atmospheric pressures. The methods are designed to provide dried material so that biological activity is maintained for long durations post manufacturing at low economic cost.

Provided is a method of preparing a powder, comprising the steps of:
- spraying a carrier liquid into a chamber to form a flow of liquid droplets, wherein the carrier liquid contains a powder-forming ingredient;
- freezing the liquid droplets into frozen particles;
- entraining the flow of frozen particles within a net flow of gas of less than about 13 SCFM, the net flow of gas entering the chamber around the flow of frozen particles to prevent the frozen particles from accumulating on the walls of the chamber;
- collecting the frozen particles on a filter;
- drying the frozen particles by passing a flow of gas downward through the frozen particles of greater than about 16 SCFM to remove the carrier liquid; and
- forming a dry powder.

Provided is a powder produced by a method comprising the steps of:
- spraying a carrier liquid into a chamber to form a flow of liquid droplets, wherein the carrier liquid contains a powder-forming ingredient;
- freezing the liquid droplets into frozen particles;
- entraining the flow of frozen particles within a net flow of gas of less than about 13 SCFM, the net flow of gas entering the chamber around the flow of frozen particles to prevent the frozen particles from accumulating on the walls of the chamber;
- collecting the frozen particles on a filter;
- drying the frozen particles by passing a flow of gas downward through the frozen particles of greater than about 16 SCFM to remove the carrier liquid; and
- forming a dry powder.

Provided is a loosely structured bed of frozen liquid particles containing a powder-forming ingredient prepared by a method comprising the steps of:
- spraying a carrier liquid into a chamber to form a flow of liquid droplets, wherein the carrier liquid contains a powder-forming ingredient;
- freezing the liquid droplets into frozen particles;
- entraining the flow of frozen particles within a net flow of gas of less than about 13 SCFM, the net flow of gas entering the chamber around the flow of frozen particles to prevent the frozen particles from accumulating on the walls of the chamber.

DETAILED DESCRIPTION

Abbreviations and Definitions

Figure 1:
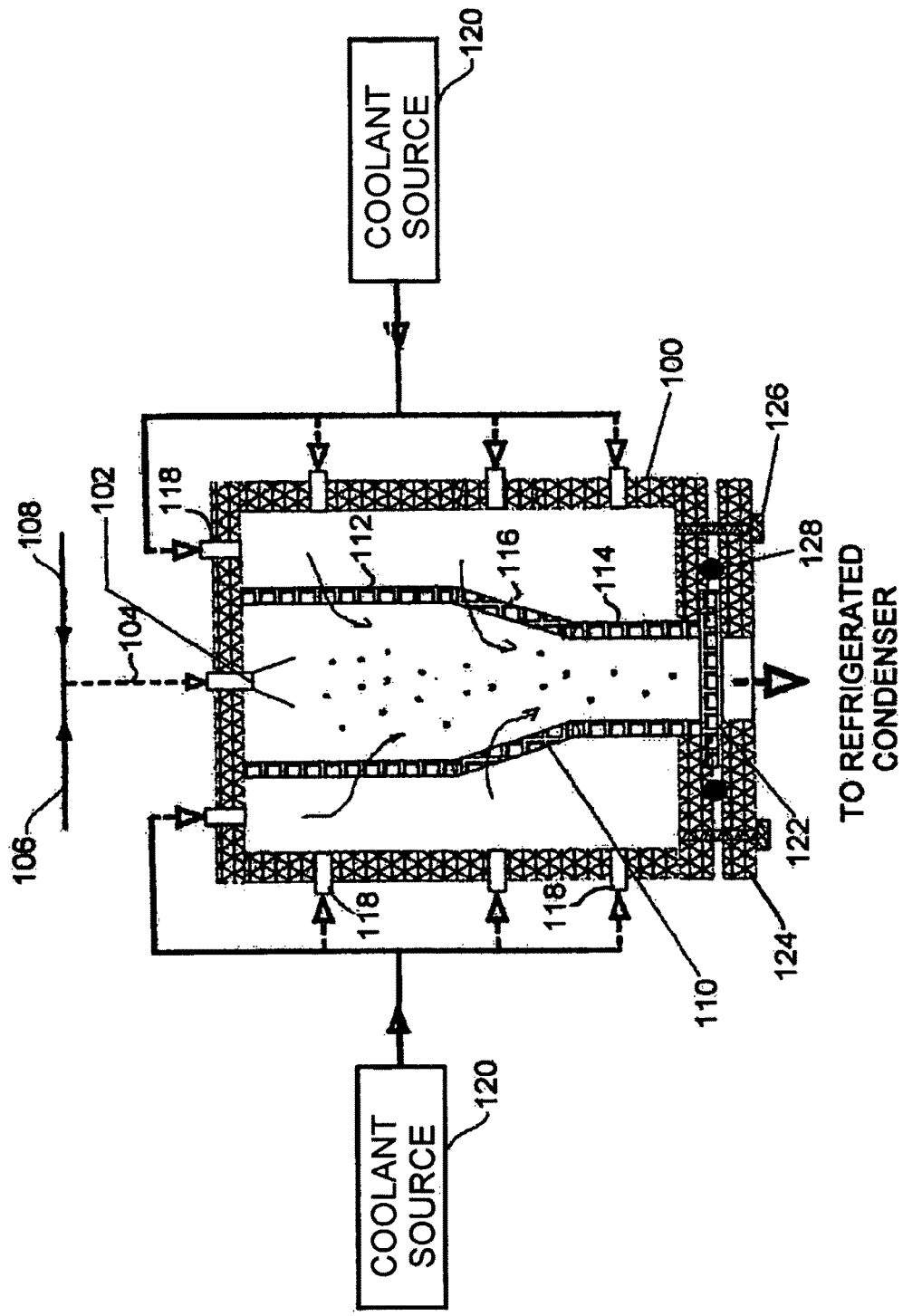
FIG. 1 shows a first embodiment of a device for accomplishing atmospheric spray freeze drying according to the invention.

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The term "powder-forming ingredient" is used to refer to one or more pharmaceutical, nutraceutical, food or other substances that can be dried from a solution into powder form by ASFD and have utility in powder form.

The term "carrier liquid" is used to refer to non-reactive liquid that carries the powder-forming ingredient. The combination of the carrier liquid and powder-forming ingredient may form a solution, emulsion or suspension.

As used herein, the term "degassing", or variations such as "degassed" or "degas" refers to the removal of at least a proportion of the gas or gases dissolved in a liquid. There are many possible methods for removing gases from liquids such as a freeze-thaw process, sonication, application of a vacuum with or without purging, where one active gas (usually oxygen) might be replaced with an inert gas (e.g., nitrogen). Filtration through a membrane has also been shown to degas liquids efficiently. In certain embodiments, solutions containing powder-forming ingredients may be degassed prior to spraying the liquid into the chamber. In certain embodiments, solutions containing powder-forming ingredients may not be degassed prior to spraying the liquid into the chamber.

The term "SCFM" is used to refer to gas flow rate in Standard Cubic Feet per Minute.

The term "powder forming ingredient" is used to refer to one or more pharmaceutical, nutraceutical, food or other substances that have utility in powder form.

Atmospheric Spray Freeze Drying (ASFD) is a process in which a liquid solution or suspension of a powder forming ingredient is sprayed as mist of fine droplets. The spray mist is cooled to a temperature below the freezing point of the solvent of the pre-spray freeze dry formulation, causing the droplets to freeze. The frozen droplets are collected, and then the solvent removed by passing a flow of gas through the frozen particles, and forming a dry powder. The process takes place at, or near atmospheric pressure. This is in contrast to sublimation (i.e., lyophilization) in a vacuum. As discussed below, the particles can be annealed (i.e. the temperature adjusted to a temperature less than the glass transition temperature of the frozen droplets) prior to drying. This can produce a spray freeze-dried powder having particles with a desired size range and characteristics, as is more fully discussed below. Suitable spray freeze drying methodologies are also described below.

The term "non-reactive" is used to refer to a gas that is substantially inert, especially vis-a-vis the carrier liquid, powder-forming ingredient, and any excipients. Preferred non-reactive gases comprise carbon dioxide, nitrogen, helium, and argon, as well as mixtures of these gases with each other or with other gasses.

A glucan molecule is a polysaccharide of D-glucose monomers, linked by glycosidic bonds. α-Glucans (alpha-glucans) are polysaccharides of D-glucose monomers linked with glycosidic bonds of the alpha form; β-Glucans (beta-glucans) are polysaccharides of D-glucose monomers linked by β-glycosidic bonds.

Dextran is an α-D-1,6-glucose-linked glucan with side-chains 1-3 linked to the backbone units of the Dextran biopolymer. The degree of branching is approximately 5%. The branches are mostly 1-2 glucose units long. Dextran is a glucose polymer in which the linkages between glucose units are almost entirely of the α(1,6) type, typically more than 95 percent. Below is a fragment of the dextran structure:

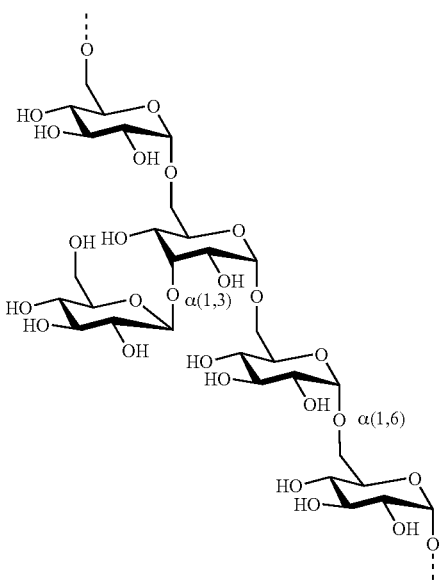

Dextran 500 refers to the polymer having an average molecular weight of about 500,000 g/mol.

The terms "loosely-packed" or "loosely structured" is used to refer to particles resting on each other so that they minimize contact between neighboring particles and maximize interstitial spaces between adjacent particles. The term "loosely" is here used in contrast with the term "tightly".

The term "cryoprotectant" as used herein, includes agents that provide stability to a biologically active compound in a formulation to militate against freezing-induced stresses. The term is used loosely and includes lyoprotectants. Conventional cryoprotectants are glycols (alcohols containing at least two hydroxyl groups), such as ethylene glycol, propylene glycol, and glycerol. Ethylene glycol is commonly used as automobile antifreeze, and propylene glycol has been used to reduce ice formation in ice cream. Dimethyl sulfoxide (DMSO) is also regarded as a conventional cryoprotectant. Glycerol and DMSO have been used for decades by cryobiologists to reduce ice formation in cells that are cold-preserved in liquid nitrogen. Some cryoprotectants function by lowering the glass transition temperature of a solution or of a material. In this way, the cryoprotectant prevents actual freezing, and the solution maintains some flexibility in a glassy phase. Many cryoprotectants also function by forming hydrogen bonds with biological molecules as water molecules are displaced. Hydrogen bonding in aqueous solutions is important for proper protein and DNA function. Thus, as the cryoprotectant replaces the water molecules, the biological material retains its native physiological structure and function, although they are no longer immersed in an aqueous environment. This preservation strategy is most often utilized in anhydrobiosis. Cryoprotectants are also used to preserve foods. These compounds are typically sugars that are inexpensive and do not pose any toxicity concerns. For example, many (raw) frozen chicken products contain a "solution" of water, sucrose, and sodium phosphates. Cryoprotectants can stabilize products such as proteins during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g. PS-20 or PS-80); and amino acids, such as glycine, arginine, leucine, and serine. A cryoprotectant exhibiting low toxicity in biological systems is generally used. The cryoprotectant, if included in the formulation, is generally added to a final concentration of between about 0.1% and about 10% (weight/volume), e.g., between about 0.5% and about 10%, between about 0.5% and about 5%, between about 0.5% and about 2%, between about 1% and about 5%, or between about 5% and about 10%.

Similar to cryoprotectants, some molecules protect freeze-dried material. Known as lyoprotectants, these molecules are typically polyhydroxy compounds such as sugars (mono-, di-, and polysaccharides), polyalcohols, and their derivatives. Trehalose and sucrose are natural lyoprotectants. The term "lyoprotectant" as used herein, includes agents that provide stability to a biologically active compound during the drying process, e.g., by providing an amorphous glassy matrix and by binding with a protein through hydrogen bonding, replacing the water molecules that are removed during the drying process. This helps to maintain a protein's conformation, minimize protein degradation during the drying cycle, and improve the long-term product stability. Non-limiting examples of lyoprotectants include sugars, such as sucrose or trehalose; an amino acid, such as monosodium glutamate, non-crystalline glycine or histidine; a methylamine such, as betaine; a lyotropic salt, such as magnesium sulfate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a formulation is generally an amount that does not lead to an unacceptable amount of degradation/aggregation of the protein when the protein formulation is dried.

The term "surfactant" as used herein, includes agents that reduce the surface tension of a liquid by adsorption at the air-liquid interface. Examples of surfactants include, without limitation, nonionic surfactants, such as polysorbates (e.g., polysorbate 80 or polysorbate 20); poloxamers (e.g., poloxamer 188); Triton™ (e.#., Triton™X-100); sodium dodecyl sulfate (SDS); sodium octyl glycoside; lauryl-sulfobetaine; myristyl-sulfobetaine; linoleyl-sulfobetaine; stearyl-sulfobetaine; lauryl-sarcosine; myristyl-sarcosine; linoleyl-sarcosine; stearyl-sarcosine; linoleyl-betaine; myristyl-betaine; cetyl-betaine; lauroamidopropyl-betaine; cocamidopropyl-betaine; linoleamidopropyl-betaine; myristamidopropyl-betaine, palmidopropyl-betaine; isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the Monaquat™ series (Mona Industries, Inc., Paterson, N.J.); polyethyl glycol; polypropyl glycol; and copolymers of ethylene and propylene glycol (e.g., pluronics, PF68). The amount of surfactant added is such that it maintains aggregation of a reconstituted protein at an acceptable level as assayed using, e.g., SEC-HPLC to determine the percentage of high molecular weight (HMW) species or low molecular weight (LMW) species, and minimizes the formation of particulates after reconstitution of a dried powder described herein. For example, the surfactant can be present in a formulation (liquid or prior to drying) in an amount from about 0.001-0.5%, e.g., from about 0.05-0.3%.

The term "bulking agent" as used herein, includes agents that provide the structure of the dried product without interacting directly with the biologically active compound. In addition to providing a pharmaceutically elegant cake, bulking agents may also impart useful qualities concerning modifying the collapse temperature, providing freeze-thaw protection, and enhancing the protein stability over long-term storage. Non-limiting examples of bulking agents include mannitol, glycine, lactose, and sucrose. Bulking agents may be crystalline (such as glycine, mannitol, or sodium chloride) or amorphous (such as dextran or hydroxyethyl starch) and are generally used in powder formulations in an amount from 0.5% to 10%.

The term "snap freezing" or "rapid freezing" or "quick freezing" as used interchangeably herein refers to freezing a solvent or solution, including solutions containing macromolecules, such as proteins, by spraying the solution into a super cooled atmosphere having a temperature well below the freezing point of the solvent or solution. "Snap freezing" and "rapid freezing" generally occur within a period of about a few milliseconds to 1-2 seconds.

Other pharmaceutically acceptable carriers, excipients, or stabilizers, such as those described in Remington: The Science and Practice of Pharmacy 20th edition, Gennaro, Ed., Lippincott Williams & Wilkins (2000) may also be included in a protein formulation described herein, if they do not adversely affect the desired characteristics of the formulation. Acceptable carriers, excipients, or stabilizers are nontoxic to recipients (e.g., patients) at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counter-ions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

In summary, cryoprotectants, lyoprotectants, surfactants, bulking agents, carriers, excipients, stabilizers or other excipients may, or may not, be added to any given formulation or solution to aid in preventing degradation of substances during or after processing. The ingredient carrying liquid may contain one, or several different biologically active compounds, along with this excipient material in various proportions. For example, a solution with lactose can be made up of mostly of lactose with only a little active compound, or there may be proportionately a large amount of active compound in the ingredient carrying liquid, plus only a small amount of lactose or other filler/matrix/excipient compound. In addition, there may be more than one active compound in the solution.

Methods

The present disclosure provides new compositions and methods for preparing dried powders. A powder-forming ingredient mixed with a liquid carrier is sprayed into a chamber, and the sprayed droplets are entrained within a low flow of gas. The droplets are frozen into solid particles that are collected on a filter at the bottom of the chamber. The frozen particles are dried by passing gas through the powder to remove the carrier liquid and leave a dry powder. A feature of this disclosure is the discovery that the low gas flow rate during spraying associated with these methods yield a loosely constructed bed of frozen liquid droplets that can be dried more efficiently than prior methods. Another feature is the discovery that the frozen particles can be dried by a gas with a temperature greater than the freezing point of the liquid carrier.

The present disclosure is especially useful for fragile and heat-sensitive substances, such as proteins, nucleic acids, oligonucleotides, enzymes, liposomes, lipids, lipid complexes, anti-virals and vaccines (e.g. involving nonvirulent or attenuated pathogens), carbohydrates, polymers, polysaccharides, and peptides. However, its use is not limited to only large molecules, since the method always produces a powder from any material dissolved or suitably suspended in a solvent. The ultimate use has nothing to do with the composition or the method. It may be used to create, for example, powder anti-infectives, anti-microbials, anti-inflammatories, antineoplastics, analgesics, anaesthetics, cholinergics, adrenergics, anticonvulsants, anti-depressants, sedatives, tranquilizers and antiemetics, immunosuppressives and immunostimulants, antihistamines, hormones, antivenoms and antitoxins. However, there may be many other non-pharmaceutical powders manufactured by this process. Cryoprotectants, lyoprotectants, surfactants, bulking agents, carriers, excipients, stabilizers or other excipients may, or may not, be added to aid in preventing degradation of substances during processing. The ingredient carrying liquid may contain several different biologically active compounds and excipient material. For example, the particles may be mostly of lactose with only a little active compound in them, or there may be several active compounds in the ingredient carrying liquid, plus lactose or other filler/matrix/excipient compound.

Powders produced via the methods described herein

Provided is a method of preparing a powder, comprising the steps of:
  a) spraying a carrier liquid into a chamber to form a flow of liquid droplets, wherein the carrier liquid contains a powder-forming ingredient;
  b) freezing the liquid droplets into frozen particles;
  c) entraining the flow of frozen particles within a net flow of gas of less than about 13 SCFM, the flow of gas entering the chamber around the flow of frozen particles to prevent the frozen particles from accumulating on the walls of the chamber;
  d) collecting the frozen particles on a filter;
  e) drying the frozen particles by passing a flow of gas downward through the frozen particles at a rate of greater than about 16 SCFM to remove the carrier liquid; and
  f) forming a dry powder.

In some embodiments, the net flow of gas may be less than about 10 SCFM, less than about 8 SCFM, or less than about 6 SCFM in step c.

In some embodiments, the net flow of gas is greater than about 15 SCFM, greater than about 20 SCFM, greater than about 25 SCFM, or greater than about 30 SCFM in step e.

The carrier liquid is selected for its ability to carry the powder-forming ingredient in the desired state, i.e., solution, emulsion or suspension. Any solvent that is inert to the powder-forming ingredient can be used as a carrier liquid and any excipient can be added to help in the process during or after the manufacturing run. Water and alcohols, and mixtures thereof are examples that may be used according to the disclosure. Water and alcohols are particularly advantageous because of their inertness and solubilizing properties for a wide range of biologically active substances.

In some embodiments, the powder-forming ingredient is suspended or dissolved in the carrier liquid prior to spraying the carrier liquid into the chamber.

In some embodiments, the gas is sprayed from a ring nozzle. In some embodiments, the gas is injected through porous walls of the chamber. In some embodiments, the gas is injected through the top of the chamber.

In some embodiments, the liquid droplets are snap frozen.

In some embodiments, the gas has an initial temperature range below the freezing temperature of the liquid particles and subsequent temperatures during drying of the frozen particles above the freezing temperature of the liquid particles.

In some embodiments, the gas has a temperature below the freezing point of the carrier liquid during freezing of the droplets and a temperature warmer than the freezing point of the carrier liquid during step e. In some embodiments, the gas has a temperature below the melting point of the carrier liquid during step e In some embodiments, the gas has a temperature greater than 3° F. above the melting point of the carrier liquid, greater than about 5° F. above the melting point of the carrier, greater than about 10° F. above the melting point of the carrier liquid, or greater than about 20° F. above the melting point of the carrier liquid during step e.

The gas may be, or may not be, any gas that does not contaminate or degrade the prepared powder. Suitable gases include nitrogen, argon, helium, carbon dioxide, and mixtures thereof. In particular embodiments, the gas comprises nitrogen. In particular embodiments, the gas comprises argon. In particular embodiments, the gas comprises carbon dioxide.

In some embodiments, the method is performed in the absence of vibration, internals, mechanical stirring, and/or agitation. In some embodiments, the method is performed in the presence of vibration, internals, mechanical stirring, and/or agitation.

In some embodiments, the carrier liquid contains more than one powder-forming ingredient. In certain embodiments, the carrier liquid contains an excipient. In particular embodiments, carrier liquid contains a cryoprotectant, lyoprotectant, surfactant, bulking agent, carrier, and/or stabilizer. In certain embodiments, the carrier liquid contains no excipient. In particular embodiments, carrier liquid contains no cryoprotectant, no lyoprotectant, no surfactant, no bulking agent, no carrier, nor a stabilizer.

In some embodiments, the net flow of freezing gas or drying gas is co-current with the flow of liquid droplets.

In some embodiments, the spraying, freezing, and entraining of the liquid droplets are carried out within the chamber.

In some embodiments, the deposition and/or drying of the frozen particles is carried out within the chamber.

In some embodiments, the deposition and/or drying of the frozen particles is carried out outside the chamber.

In some embodiments, the drying of the frozen particles is carried out outside the chamber.

In some embodiments, the frozen liquid droplets have a median diameter of about 250 μm (microns) or less, about 100 μm (microns) or less, about 75 μm (microns) or less, about 50 μm (microns) or less, about 25 μm (microns) or less, about 10 μm (microns) or less, or about 1 μm (microns) or less.

In some embodiments, the powder-forming ingredient is suspended or dissolved in the carrier liquid at a concentration greater than about 2 wt %, greater than about 5 wt %, greater than about 10 wt %, greater than about 20 wt %, greater than about 30 wt %, or greater than about 40 wt % prior to spraying the carrier liquid into the chamber.

The biologically active agents may be encapsulated in a liposome. Liposomes are formed when suitable amphophilic molecules are allowed to swell in water or aqueous solutions to form liquid crystals usually of multi-layer structure comprised of many bilayers separated from each other by aqueous material.

In the embodiments shown in FIG. 1, a flow or spray of atomized carrier fluid is frozen into a powder of solid particles by an entraining flow of cold gas. Entraining by the cooling gas provides for confining the spray and immediate freezing of the individual spray droplets, so that the liquid spray droplets do not impact the walls of the chamber.

Figure 2:
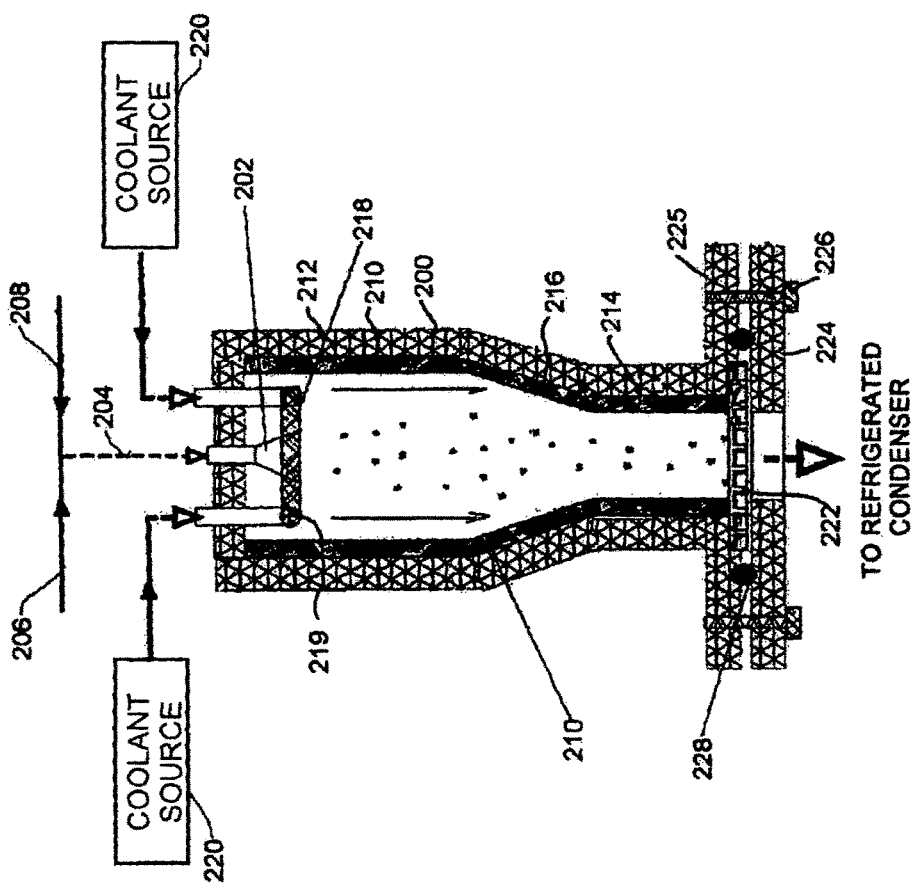
FIG. 2 shows a second embodiment of a device for accomplishing atmospheric spray freeze drying according to the invention.
Figure 3:
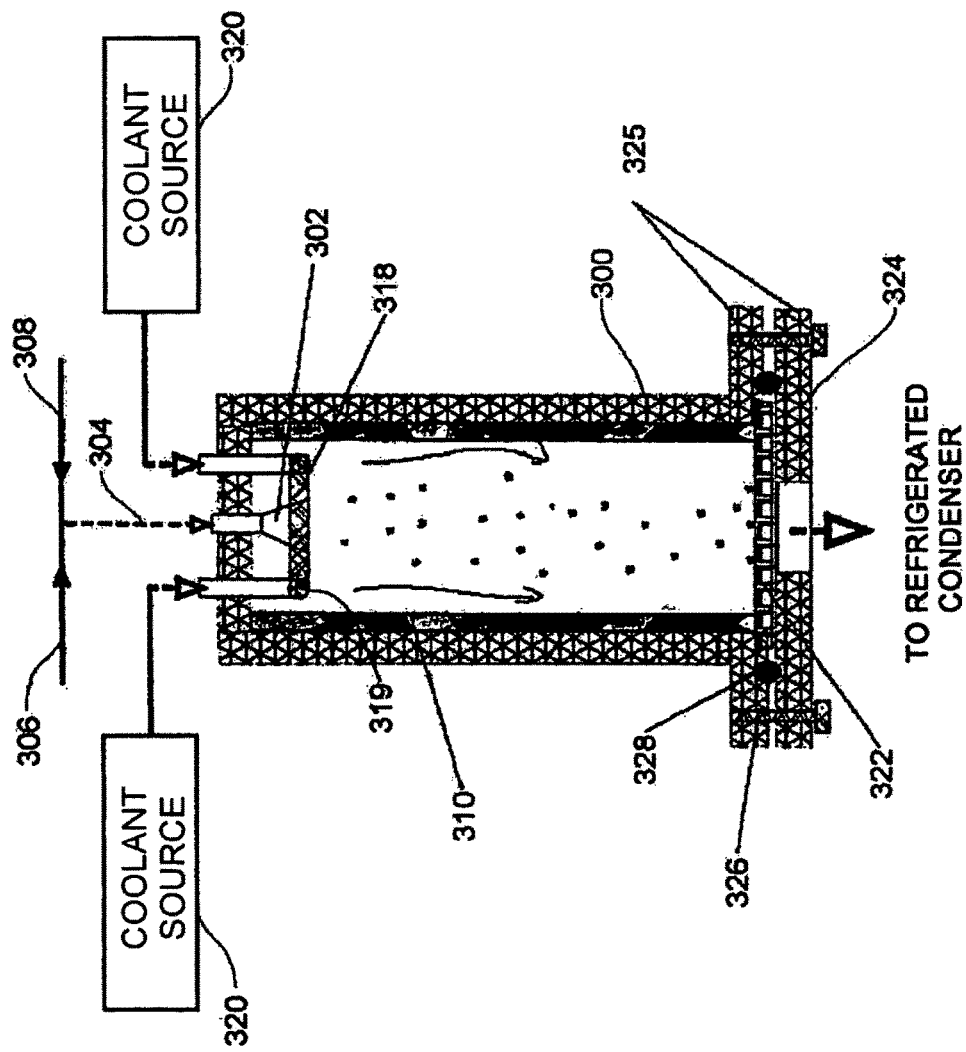
FIG. 3 shows a third embodiment of a device for accomplishing atmospheric spray freeze drying according to the invention.

In certain embodiments, the powder-forming ingredients are mixed with a carrier liquid prior to spraying from the atomizer 102, 202, or 302. The spray fluid resulting from the mixture may be, for example, a solution, a suspension or a colloid. The atomizer 102, 202, 302 may be a two-fluid nozzle or an ultrasonic nebulizer or a vibrating orifice aerosol generator (VOAG) or some other atomizing device. The spray fluid, which is formed of liquid droplets, is rapidly frozen through contact with cold gas of a suitable temperature. In the spray-freeze step, cooling fluid may be supplied in several possible ways. One way, shown in FIGS. 2, 3, is to spray cooling liquid such as liquid nitrogen directly into the chamber 200, 300 by using the ring nozzle 218, 318, while spray droplets from atomizer 202, 302 inside the perimeter of the ring nozzle 218, 318 are frozen immediately after contacting the surrounding curtain of liquid nitrogen and then conveyed to the exit filter 222, 322 at the exit end of the housing 200, 300. Alternatively, a cooling gas may also be sprayed from the top of the chamber through a porous top piece. Another approach, shown in FIG. 1, is to have a cooling gas enter through porous walls 112, 114, 116 that enclose the atomizer 102. Gas supplied into the space between the housing 100 and chamber 110 forms a gas jacket whose temperature is adjusted by mixing with nitrogen gas from liquid nitrogen or an equivalent cryogenic at different ratios.

The flow of cold gas during freezing is sufficiently low to yield a loosely structured bed of frozen liquid droplets in order to maximize interstitial spaces around each particle. The liquid carrier is then removed from the frozen liquid droplets and absorbed by the drying gas by convection drying. This low-density lattice of particles maximizes the flow of desiccating gas around the particles. As a result, carrier molecules move from a frozen solid phase through a liquid phase and into a gas phase.

This approach contrasts with earlier methods that employ higher gas flow rates during the freezing step. The higher flow rates employed in the earlier methods create a densely packed bed of frozen liquid particles that impedes the desiccating gas flow around the particles. Since the carrier vapor is swept away more slowly, the drying rate is decreased. This also differs from other earlier methods where gas flows lift particles upwards due to an upwards flow of drying gas fluidizing the frozen particles upwards from the particle bed.

In some embodiments, the liquid droplets are frozen in a cooled gas net gas flow of less than about 13 SCFM. In some embodiments, the net flow of gas is less than about 10 SCFM. In certain embodiments, the net flow of gas is less than about 8 SCFM. In particular embodiments, the net flow of gas is less than about 6 SCFM.

Initially the carrier solvent vapor moves off the surface of the frozen particles. After all the surface carrier vapor has moved off the surface of the particles, it must diffuse from the particle interior to the surface to move into the gas phase.

After completion of the spray-freezing process at around −100° C., the temperature of the gas flow may be warmed, and the net flow of gas increased. Although initial drying takes place at a temperature below the freezing point of the carrier, higher temperatures above the freezing temperature speed the drying of the frozen particles. Evaporation is controlled to maintain the frozen core of the particles, even when the surrounding gas flow is warmer than the melting point of the carrier liquid within the frozen particles. Temperature increases are timed to avoid melting the carrier liquid within the frozen particles before drying is complete. Significant particle melting that occurs during the process, termed "meltback," causes the loosely structured particles to adhere in a dense and distorted bed of fused particles, inhibiting the rapid flow of desiccating gas around the particles. As a result, the drying rate is slow and uneven across the fused bed of particles.

In some embodiments, a loosely structured bed of frozen liquid droplets is dried in a gas flow of greater than about 15 SCFM. In some embodiments, the net flow of gas is greater than about 20 SCFM. In certain embodiments, the net flow of gas is greater than about 25 SCFM. In some embodiments, the net flow of gas is greater than about 30 SCFM. In particular embodiments, the net flow of gas is greater than about 35 SCFM.

In some embodiments, the net flow of gas has a temperature within the temperature range during freezing of the liquid particles and a temperature warmer than the first temperature range during drying of the frozen particles. In certain embodiments, the net flow of gas has a temperature below the freezing point of the carrier liquid during freezing of the droplets and a temperature warmer than the freezing point of the carrier liquid during drying of the frozen particles. In particular embodiments, the net flow of gas has a temperature between about 0° and 3° F. during drying of the frozen particles. In particular embodiments, the net flow of gas has a temperature between about 2° and 5° F. during drying of the frozen particles. In particular embodiments, the net flow of gas has a temperature greater than about 8° F. during drying of the frozen particles. In particular embodiments, the net flow of gas has a temperature greater than about 10° F. during drying of the frozen particles. In particular embodiments, the net flow of gas has a temperature greater than about 20° F. during drying of the frozen particles.

In some embodiments, the method is performed in the absence of vibration, internals, or mechanical stirring. In some embodiments, the method is performed in the absence of vibration, internals, or mechanical stirring.

In some embodiments, the deposition and drying of the frozen particles is carried out within the chamber. In some embodiments, drying of the frozen particles is carried out outside the chamber.

The process yields dry porous particles often approximately the same size and shape as the original frozen droplets. In some embodiments, the frozen liquid droplets have a median diameter of about 250 μm or less. In some embodiments, the frozen liquid droplets have a median diameter of about 100 μm or less. In some embodiments, the frozen liquid droplets have a median diameter of about 75 μm or less. In certain embodiments, the frozen liquid droplets have a median diameter of about 50 μm or less. In particular embodiments, the frozen liquid droplets have a median diameter of about 25 μm or less. In particular embodiments, the frozen liquid droplets have a median diameter of about 10 μm or less. In particular embodiments, the frozen liquid droplets have a median diameter of about 1 μm or less. However, there can be considerable variation based on the nature, type, and size of the nozzle.

Compositions

In some embodiments, the powder comprises porous particles having a median porosity greater than about 50-volume %. In some embodiments, the powder comprises porous particles having a median porosity greater than about 40-volume %. In some embodiments, the powder comprises porous particles having a median porosity greater than about 30-volume %. In some embodiments, the powder comprises porous particles having a median porosity greater than about 20-volume %. In some embodiments, the powder comprises porous particles having a median porosity greater than about 10-volume %. In some embodiments, the powder comprises porous particles having a median porosity greater than about 5-volume %. In some embodiments, the powder comprises porous particles having a median porosity greater than about 1-volume %.

In some embodiments, the powder comprises a glucan. In certain embodiments, the powder comprises an alpha glucan. In certain embodiments, the powder comprises a beta glucan. In certain embodiments, the powder comprises dextran. In particular embodiments, the powder comprises dextran 500.

The low net gas flow rates during spray associated with these methods yield a loosely structured bed of frozen liquid droplets that may be dried more efficiently than prior methods. Provided is a loosely structured bed of frozen liquid particles containing a powder-forming ingredient prepared by a method comprising the steps of:

spraying a carrier liquid into a chamber to form a flow of liquid droplets, wherein the carrier liquid contains a powder-forming ingredient;

freezing the liquid droplets into frozen particles;

entraining the flow of frozen particles within a net flow of gas of less than about 13 SCFM, the net flow of gas entering the chamber around the flow of frozen particles to prevent the frozen particles from accumulating on the walls of the chamber.

In some embodiments, the bed has a density of less than about 0.50 g/cm$^3$. In some embodiments, the bed has a density of less than about 0.30 g/cm$^3$. In some embodiments, the bed has a density of less than about 0.20 g/cm$^3$. In some embodiments, the bed has a density of less than about 0.10 g/cm$^3$.

In order that the disclosure described herein may be more fully understood, the following examples are set forth. It should be understood that these examples are for illustrative purposes only and are not to be construed as limiting this disclosure in any manner.

EXAMPLES

In the embodiments shown in FIGS. 1, 2, and 3, a flow of coolant freezes a flow or spray of atomized carrier fluid and entrains the solid particles onto a filter. The powder is subsequently dried without a vacuum during primary drying by a flow of desiccating gas from top to bottom through the entrained powder on the filter. The cooling gas confines the spray, and freezes the individual spray droplets, so that the liquid spray is directed downwards onto the horizontal filter below at atmospheric pressure.

Referring to the first embodiment shown in FIG. 1, a housing 100 formed with solid insulated walls supports at an inlet end an atomizer 102 that is supplied through line 104 with compressed gas from source 106 and a suitable carrier liquid from source 108. Inside the housing 100 is a flow chamber 110 with porous walls. The flow chamber 110 is formed of cylindrical sections 112, 114 of differing diameter joined by a conical section 116. Multiple nozzles 118 of a nozzle system penetrate the housing 100 and supply a cryogenic flow of coolant from a coolant source 120 into the space between the housing 100 and flow chamber 110. At the other, exit end of the housing 100 from the atomizer 102, the flow chamber 110 terminates in a filter 122 that is held across an opening in the housing 100 by a plate 124 fixed to the chamber 100 by bolts or clamps 126 with O-ring 128. Gas flow from the exit end of the housing 100 is returned to a refrigerated condenser that forms part of the coolant source 120. The refrigerated condenser strips moisture from the cooling gas for re-use of the cooling gas.

Referring to a second embodiment shown in FIG. 2, a housing 200 formed with solid insulated walls supports at an inlet end an atomizer 202 that is supplied through line 204 with compressed gas from source 206 and a suitable carrier liquid from source 208. Inside the housing 200 is a flow chamber 210 defined by solid walls lining the housing 200. The flow chamber 210 is formed of cylindrical sections 212, 214 of differing diameter joined by a conical section 216. Surrounding the atomizer 202 is a nozzle system in the form of a ring nozzle 218, with openings 219 directing flow from the ring nozzle 218 parallel to flow from the atomizer 202. The ring nozzle 218 supplies a cryogenic flow of coolant from a coolant source 220, for example a liquid nitrogen Dewar driven by compressed gas that surrounds flow from the atomizer 202 in the spray-freezing step and a refrigerated condenser in the following drying step. At the other, exit end of the housing 200 from the atomizer 202, the flow chamber 210 terminates in a filter 222 that is held across an opening in the housing 200 by a plate 224 fixed to flanges 225 on the chamber 200 by bolts or clamps 226 with O-ring 228.

Referring to a third embodiment shown in FIG. 3, a housing 300 formed with solid insulated walls supports at the inlet end an atomizer 302 that is supplied through line 304 with compressed gas from source 306 and a suitable carrier liquid from source 308. Inside the housing 300 is a cylindrical flow chamber 310 defined by solid walls lining the housing 300. Surrounding the atomizer 302 is a ring nozzle 318, with openings 319 directing flow from the ring nozzle 318 parallel to flow from the atomizer 302. The ring nozzle 318 supplies a cryogenic flow of coolant from a coolant source 320, for example a liquid nitrogen Dewar driven by compressed gas that surrounds flow from the atomizer 302 in the spray-freezing step and a refrigerated condenser in the following drying step. At the other, exit end of the housing 300 from the atomizer 302, the flow chamber 310 terminates in a filter 322 that is held across an opening in the housing 300 by a plate 324 fixed to flanges 325 on the chamber 300 by bolts or clamps 326 with O-ring 328.

The coolant source 120, 220 or 320 may be any source of a coolant that does not contaminate or degrade the powder. Cold gas may be used such as refrigerated nitrogen, particularly for the embodiment shown in FIG. 1. Thus, the nitrogen may be obtained from liquid nitrogen or a nitrogen cylinder of compressed gas, particularly for the embodiment shown in FIGS. 2 and 3. Upon exiting the nozzles 118, 218 and 318, cold gas or liquid, for example cold liquid nitrogen or cold gaseous nitrogen, which may be sourced from a cylinder of liquid nitrogen or other cryogenic source of nitrogen, will entrain the spray and freeze the liquid drops of the spray. For freezing followed by drying, both a liquid nitrogen source and a refrigeration unit may be used. Freezing may be carried out using the liquid nitrogen source, as in the embodiment of FIGS. 2 and 3, and then drying may be carried out at warmer temperatures using the refrigeration unit.

During manufacture, pharmaceutical agents (PA) or other powder-forming ingredients are mixed with a carrier liquid prior to spraying from the atomizer 102, 202, 302. The atomizer 102, 202, 302 may be a two-fluid nozzle or an ultrasonic nebulizer or a vibrating orifice aerosol generator (VOAG) or other atomizing device. The spray fluid, which is formed of liquid droplets, is rapidly frozen through contact with coolant, which is a cold fluid of a suitable temperature. In the spray-freeze step, cooling fluid may be supplied in several possible ways. One way, shown in FIGS. 2, 3, is to spray cooling liquid such as liquid nitrogen directly into the chamber 200, 300 by using the ring nozzle 218, 318, while spray droplets from atomizer 202, 302 inside the perimeter of the ring nozzle 218, 318 are frozen immediately after contacting the surrounding curtain of liquid nitrogen and then conveyed to the exit filter 222, 322 at the exit end of the housing 200, 300. Another way, shown in FIG. 1, is to have a cooling gas enter through porous walls 112, 114, 116 that enclose the atomizer 102. Gas supplied into the space between the housing 100 and chamber 110 forms a gas jacket whose temperature is adjusted by mixing with liquid nitrogen or an equivalent cryogenic fluid at different ratios.

In the example of FIGS. 2 and 3, the curtain of spraying liquid nitrogen is used for freezing the spraying liquid droplets and avoiding cohesion of frozen powder on the sidewalls 210, 310. The spraying velocity and quantity of liquid nitrogen is controlled to meet both the cooling demand of the spray-freeze process and conveying of frozen powders to the exit filter with minimal packing of the powder 222, 322. In the example of FIG. 1, the flow passing through the porous sidewalls of the freezing chamber 110 has the same function as the spraying curtain of liquid nitrogen, i.e., reducing the particle cohesion and allowing a distinguishingly radial flow of cooling fluid into the chamber 110 to freeze liquid droplets and protect the liquid droplet/frozen particles from contacting the wall surface. The thickness of the porous sidewall 110 and pressure inside the gas jacket, which is controlled by the flow rate of cooling gas into the chamber 100, are adjusted for the particular powder being processed. Thereafter, a down-flow transport by virtue of the spray direction of the atomizer 102 is automatically formed in the spray-freeze process to carry all the frozen powder to the exit end of the chamber 100.

After the accomplishment of spray freezing, a proper drying temperature will be chosen in a drying step by flow rate adjustment from the cooling cryogenic or refrigeration system. The low-density frozen powder collected on the exit filter 122, 222, 322 at exit end (bottom) of the chamber is initially dried in a cold desiccated gas stream at atmospheric pressure. Because the low-density frozen powder maximizes the interstitial space between the particles, the dry gas flows freely around the particles, removing the frozen carrier liquid at a high rate.

The partially dried particles form a loose pile of powder on the exit filter 122, 222, 322, from which the remaining moisture is removed using a desiccated gas stream, resulting in free-flowing powders. The rapid drying cools the loose particles, and inhibits melting and refreezing of the particles. This effect may be a reason why the process can be carried out at temperatures warmer than the freezing point of the carrier liquid.

Figure 4:
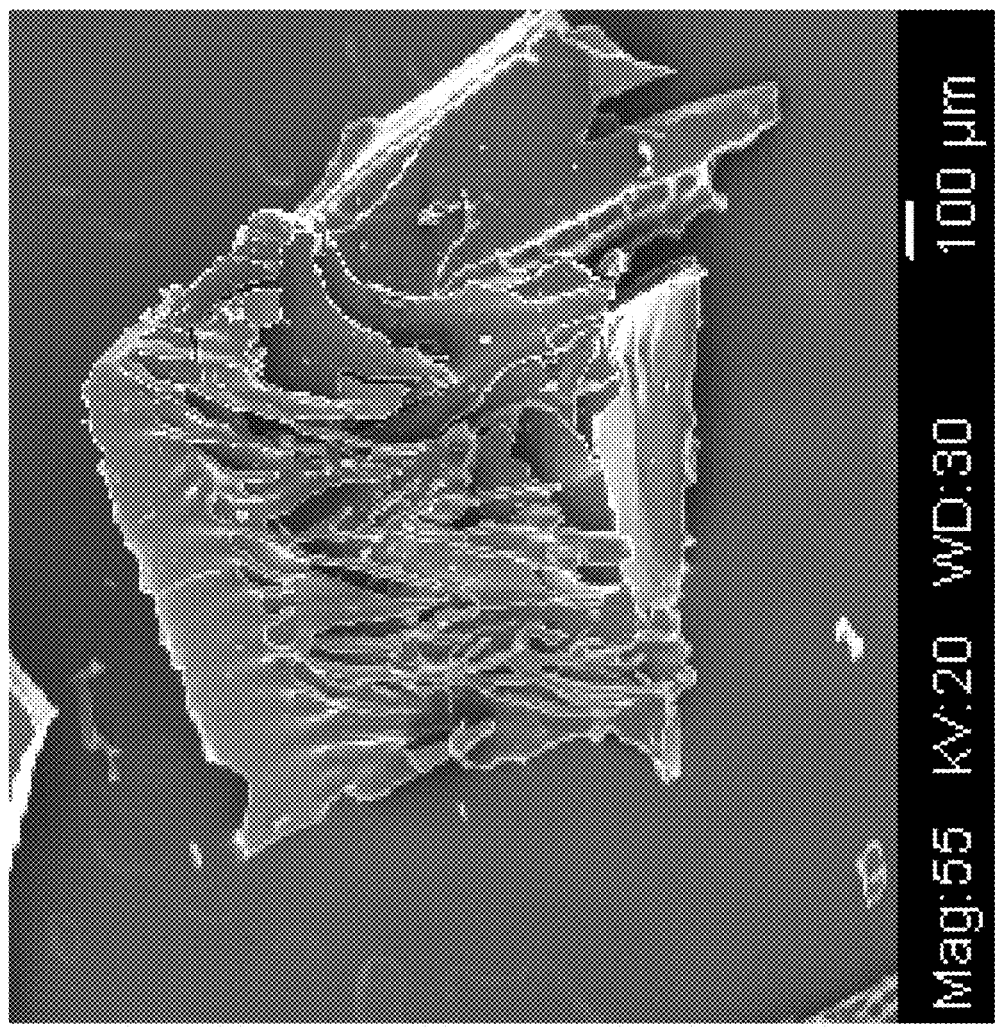
FIG. 4 shows Bovine Serum Albumin (BSA) lyophilized powder as manufactured and received from supplier and magnified 30×.
Figure 5:
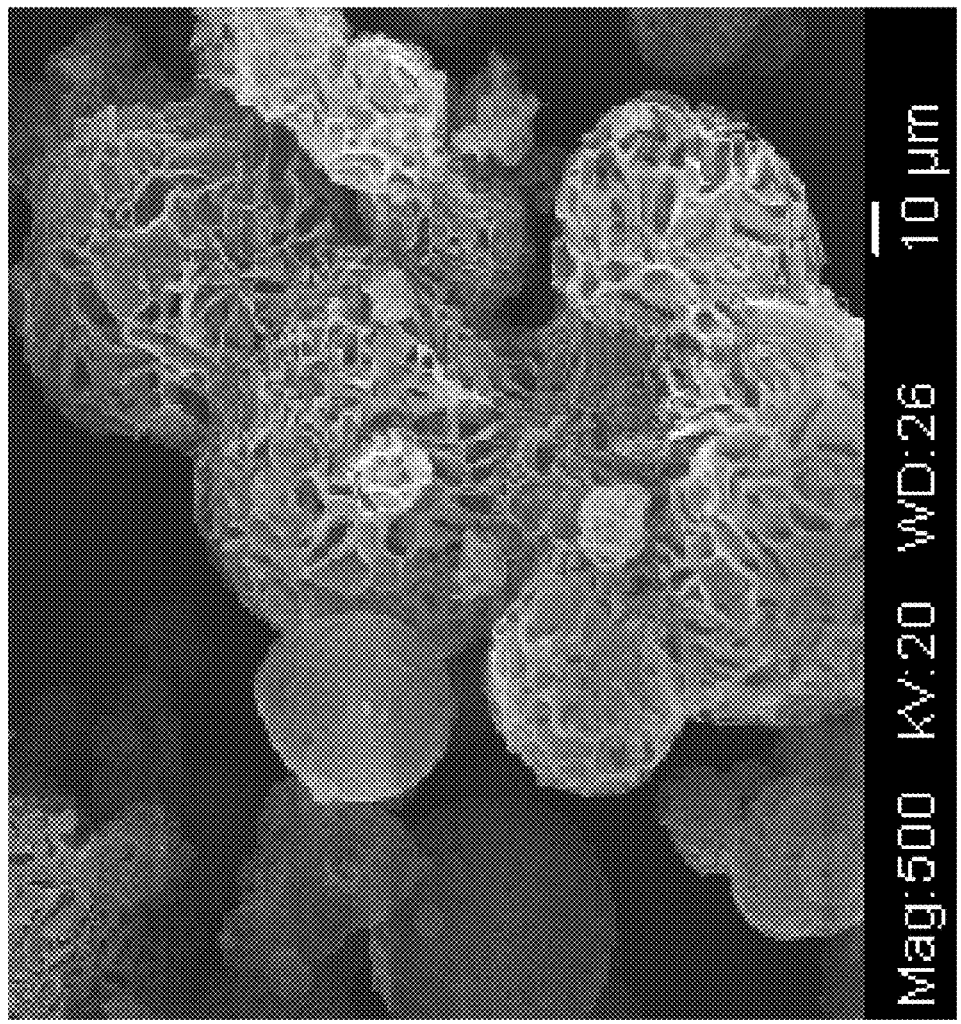
FIG. 5 shows dried BSA powder from an aqueous solution of 10% following 3.5 hour drying period per the ASFD method described herein and magnified 500×.
Figure 6:
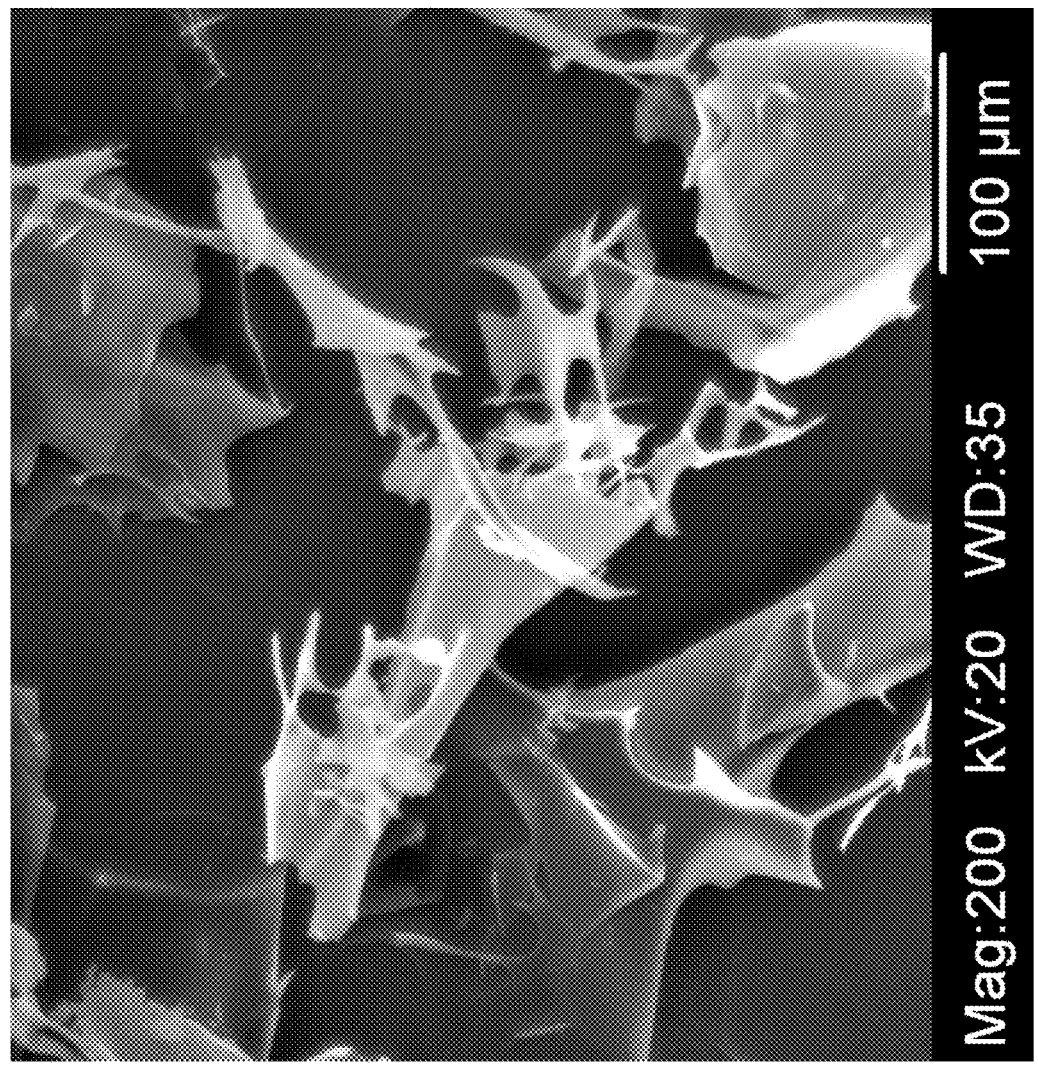
FIG. 6 shows Bovine Gamma Globulin (BGG) lyophilized powder as manufactured and received from supplier and magnified 200×.
Figure 7:
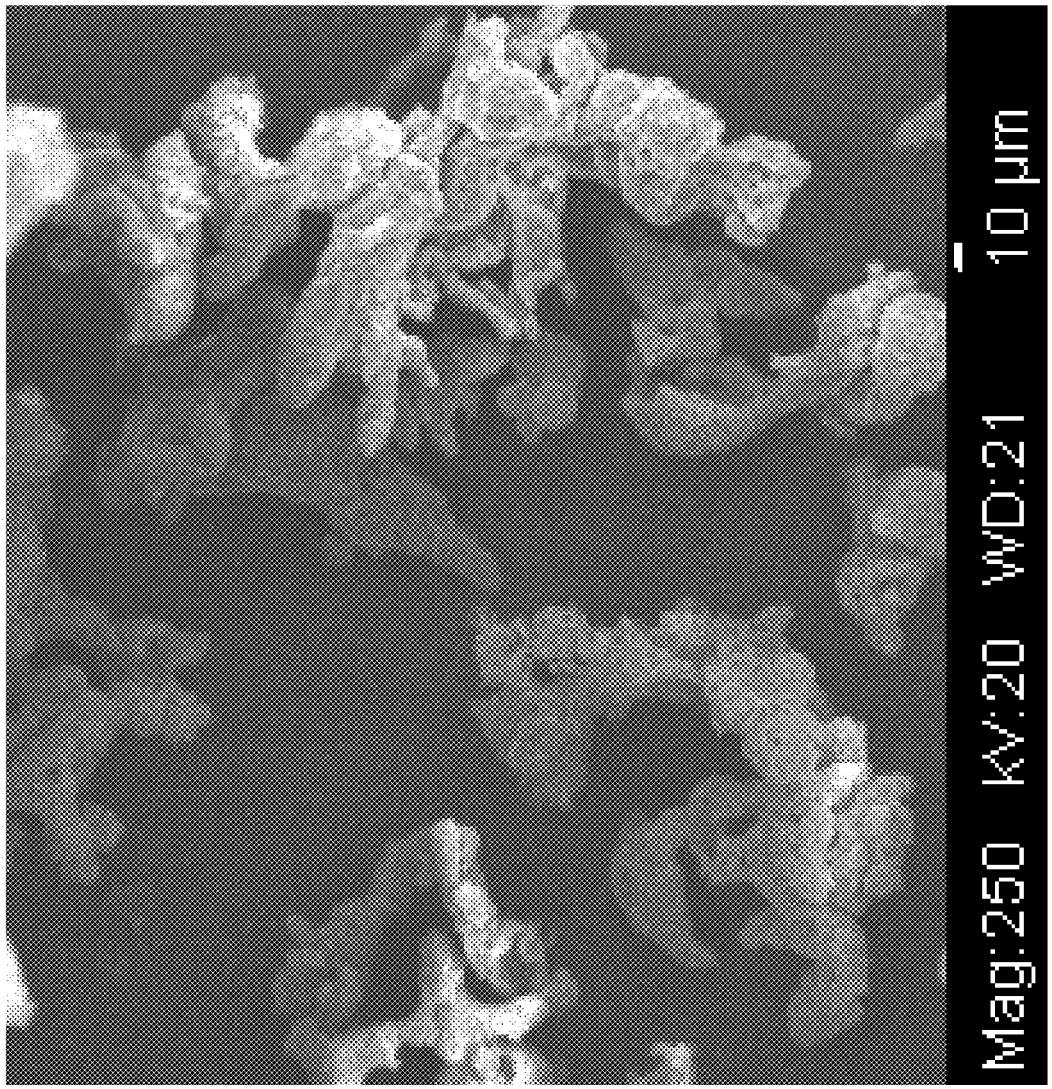
FIG. 7 shows dried BGG powder from an aqueous of 10% following a 3.5-hour drying period with the ASFD method described herein and magnified ×250.

After spray-freeze atmospheric drying, dry porous particles of roughly the same size and shape as the original frozen droplets are obtained in most cases. However, variation may occur due to the nature, type, and size of the nozzle. See FIGS. 4, 5, and 6.

Operating Procedures for the Original Equipment

The apparatus is allowed to run for approximately 5 to 15 minutes to reach the desired temperature in the chamber 110, 210, 310 via gas cooled by a refrigeration system providing gas flow into the chamber 110 through the porous wall. The aqueous solution or suspension of the substances to be dried is then sprayed using the atomizer 102, 202, 302 and frozen simultaneously at a chosen temperature by the surrounding curtain of liquid nitrogen generated from ring nozzle 218, 318 or an equivalent such as cryogenic flow from nozzles 118 through porous sidewalls of chamber 110. The frozen powder is conveyed down to the exit filter 122, 222, 322 by the concurrent downstream flow. After spray freezing, drying begins. The frozen powder collected on the exit filter 122, 222, 322, at the bottom is dried continuously at atmospheric pressure until the target moisture of the frozen powder is removed by the cold desiccated gas stream. After atmospheric spray-freeze drying, a loose powder remains on the exit filter 122, 222, 322. This powder can easily be broken up into free flowing, dry porous particles usually of approximately the same size and shape as the original frozen droplets.

In one example, powder was produced using the method described above. A 15 wt % mannitol solution was spray freeze-dried using the apparatus shown in FIG. 1. A 15 wt % mannitol (Mannitol USP powder, Fisher Scientific) aqueous solution was used to demonstrate the process. Before spraying, the chamber 110 for spray-freeze drying was allowed to run for approximately 15 minutes to reach the desired temperature (−100° C.). During the 20 minutes, the cold fluid from a refrigeration unit incorporating two parallel dry ice cooling columns flows into the chamber 110 through the porous sidewall. A Chem-Tech pump (Model CTPA4LSA-PAP1-XXXX, Viking pump of Canada Inc, Windsor, Ontario, Canada) was used to pump 20 mL of 15 wt % mannitol solution into an air atomizing spray nozzle 102 (Spraying Systems Co., Wheaton, Ill., USA) spraying into the chamber from the top with the aid of a compressed driving gas (nitrogen) at a flowrate of 0.6 SCFM. The spray-freezing process was finished within 4 minutes and meanwhile, the temperature in the chamber 110 was kept at −50° C. to −70° C. by the mixed cooling gas (nitrogen). In this case, the pressure in the chamber was almost atmospheric (around 1.02 atm). After the completion of spray-freeze process, the pump and driving gas for spraying was shut down and the cooling gas for drying was decreased so that the chamber was kept at around −15° C. (−5° C. to −20° C.) by adjusting the height of dry ice in the cooling columns. After drying for 1 hr, the temperature in the chamber was gradually raised to room temperature within another 30 minutes at a flowrate of 30 L/min. Thereafter, the cooling gas was shut off and a dry powder cake on the exit filter 122 was collected. This cake was easily broken into a free-flowing powder and the resulting particles were found to be very porous and roughly spherical. The moisture content was measured to be only 0.9 wt %. Photos from a scanning electron microscope (SEM) of one resulting sample powder collected from the exit filter showed that the powder particles are relatively spherical and considerably porous.

Mannitol has been spray-frozen at −80° C. to −100° C. and dried in a temperature of −5° C. to −20° C. in order to avoid mannitol crystallization (mannitol hydrate occurs at around 38° C.). Based on the practical reality (each biosubstance may have its ideal spray-freeze and drying temperature), the spray-freeze drying conditions are adjustable by changing the temperature and flow rate of the mixed cold gases. Depending on the batch scale, these parameters may be different.

For atmospheric spray freeze-drying with dry gas, the temperature at which material can freeze-dried is determined by its freezing point. Since the vapor pressure of ice is fixed by the freezing temperature, the resistance to water vapor diffusion in the material has an important effect on the rate of freeze-drying. Drying is also proportional to the diffusion path length, the permeability of the material, and the gradient. Atmospheric spray freeze-drying should therefore be feasible in a wide variety of materials where these conditions are very favorable.

Operating Procedures for the Second Generation Equipment

Cool Down and Spray. Cooling gas of approximately −115 to −130° C. for rapid cool down is directed through a porous tube of a chamber similar to FIG. 1. When the chamber reaches a desired temperature of about −115° C., the net flow of gas is slowed to approximately 5 SCFM, the carrier liquid containing a powder-forming ingredient is sprayed into the chamber at atmospheric pressure, and the frozen particles are collected on a filter. In specific, the equipment has a nozzle and incoming piping for solution and gas that are similar to structures 104, 106, and 108 of FIG. 1.

Drying. The loosely structured bed of frozen liquid particles, containing a powder-forming ingredient, is dried using a flow of approximately 20 SCFM flow of gas as it sits on a filter like that numbered 122 in FIG. 1. The temperature of the gas is increased from a temperature below the freezing point of the carrier liquid to a temperature greater than the melting point of the carrier liquid.

The initial drying rate and the moisture content of the exit gas rise sharply as the temperature increases. The peak rate then decreases linearly with time. It typically plateaus in the range of 200 to 400 ppm $H_2O$ after 90 minutes. No vacuum is utilized during this method.

Bovine Serum Albumin

Figure 8:
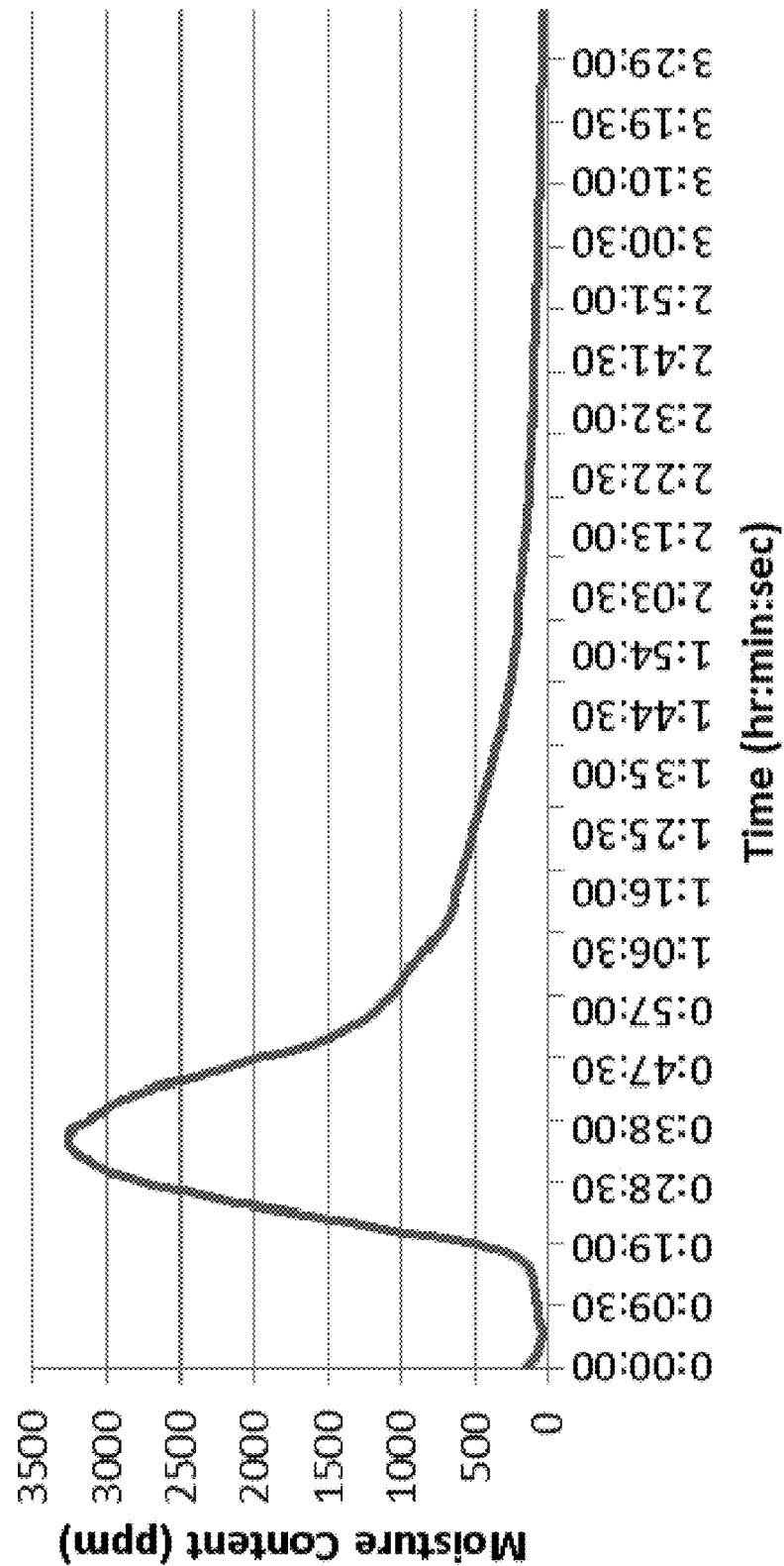
FIG. 8. shows a typical drying curve for BSA dried from an aqueous 10% solution with the ASFD method described herein.
Figure 9:
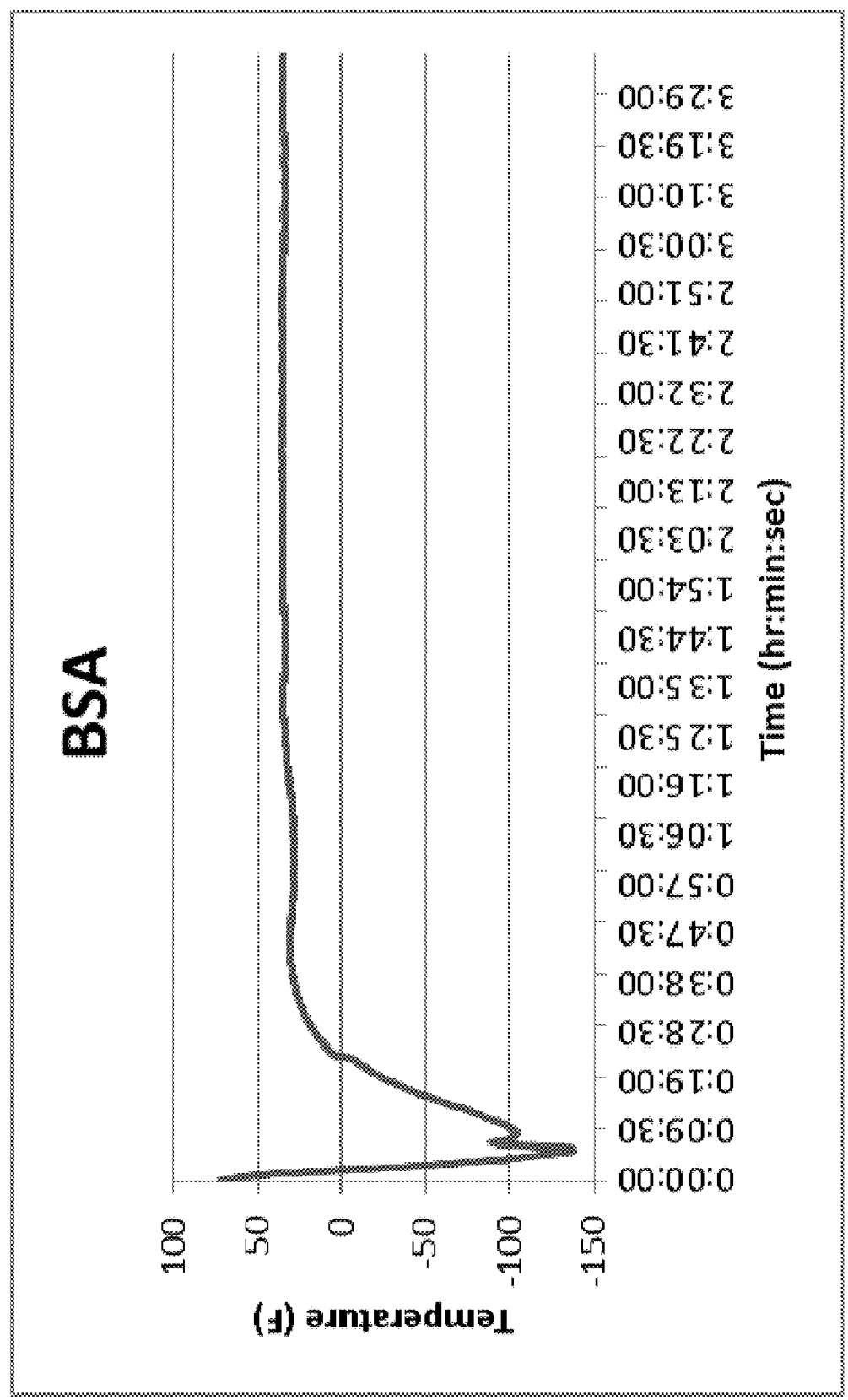
FIG. 9. shows a temperature curve for BSA dried from an aqueous 10% solution with the ASFD method described herein.

A typical ASFD run to dry Bovine Serum Albumin (BSA) was conducted per a stepwise procedure like the following example. A solution of BSA was prepared such that the BSA constituted 10% by weight of an aqueous solution. Once the inner chamber was cooled to a temperature of −140° F., 50 ml of solution was sprayed at a rate of 1 ml per second and at a pressure of 40 psi into the reactor chamber after the flow of cooling gas had been decreased to 5 SCFM. A flow rate of 20 SCFM was then set for drying. Temperature during the first hour was set at 30° F., and increased by five degrees for the rest of the run. FIG. 8 shows the amount of water in parts per million coming through the filter and as measured at the exit hose. FIG. 9 shows the temperature of the drying gas as recorded by the thermocouple nearest the filter. After three hours the powder was removed from the chamber and tested for water content. Testing showed a moisture content of 1.25%.

Bovine Gamma Globulin

Figure 10:
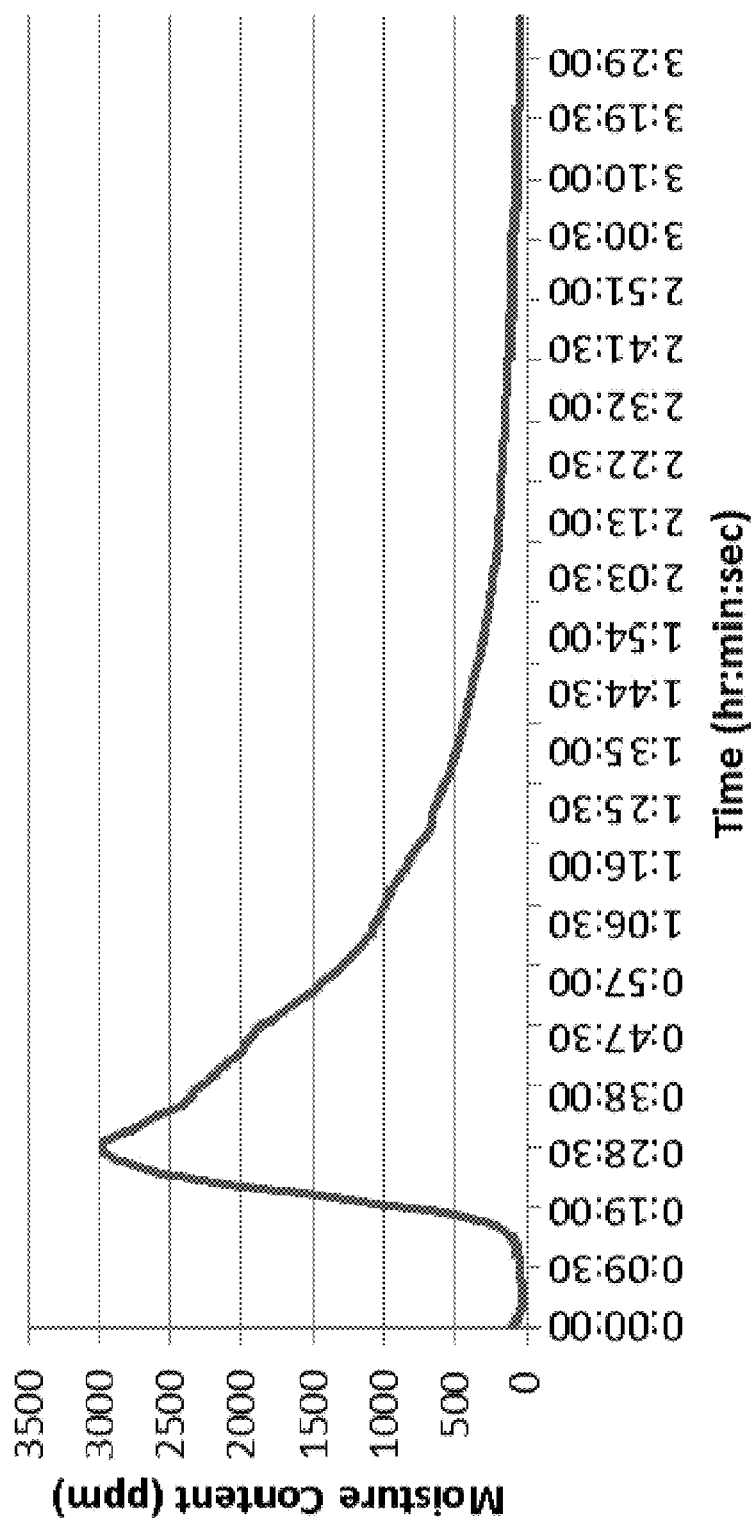
FIG. 10. shows a typical drying curve for BGG dried from an aqueous 10% solution with the ASFD method described herein.
Figure 11:
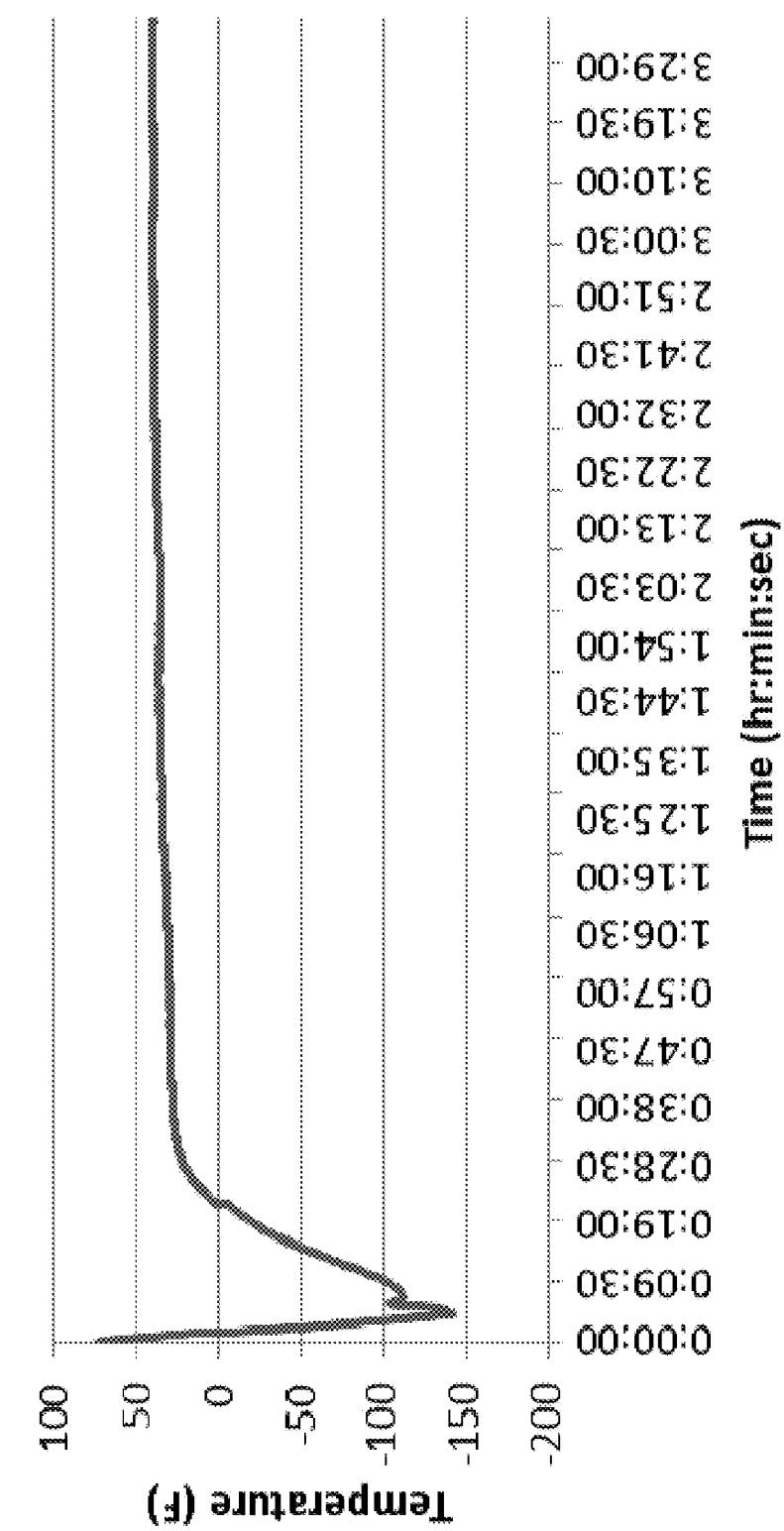
FIG. 11. shows a temperature curve for BGG dried from an aqueous 10% solution with the ASFD method described herein.
Figure 12:
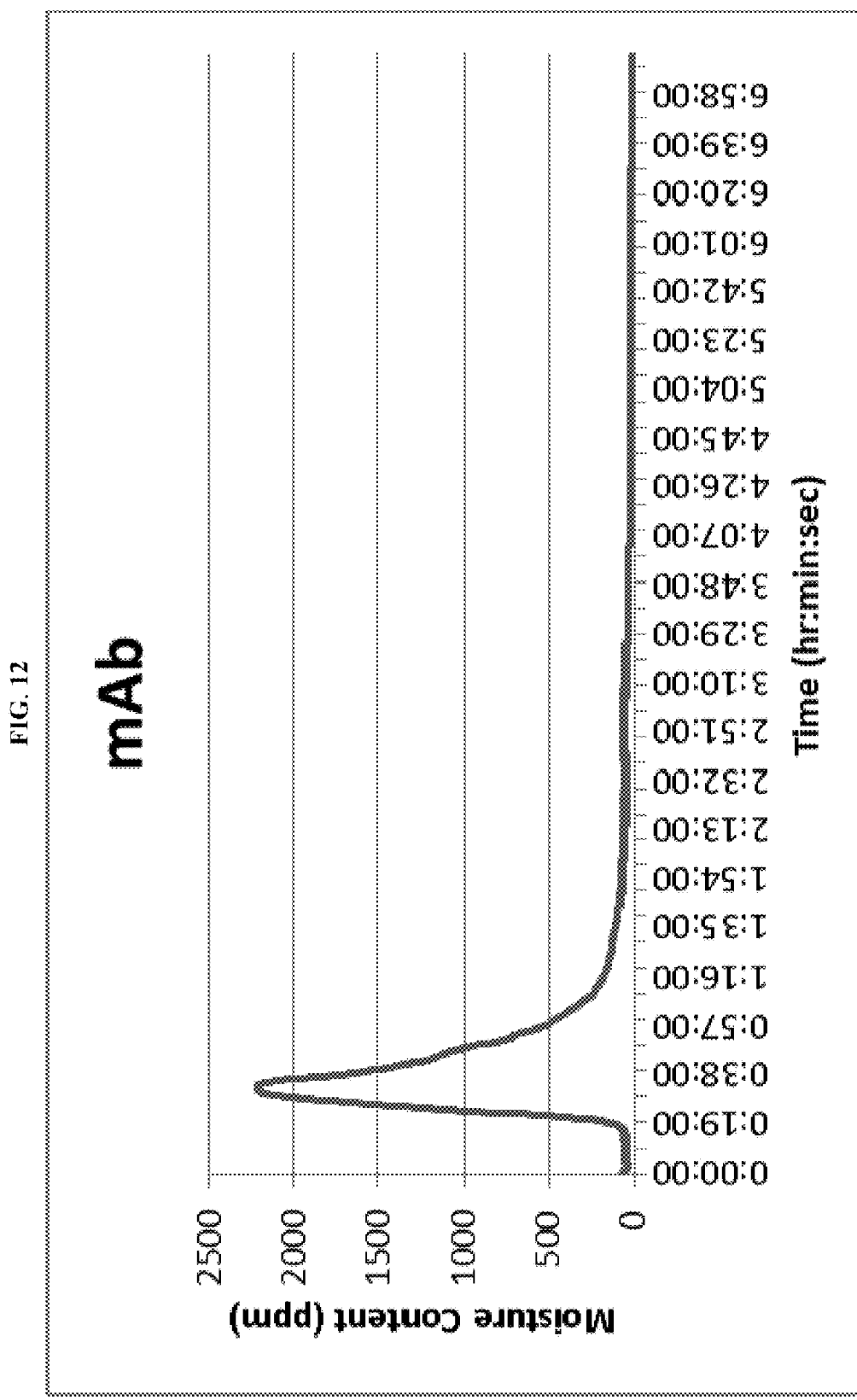
FIG. 12. shows a typical drying curve for a monoclonal antibody (mAb) dried from an aqueous solution comprising 12% mAb and 4.6% cryoprotectants by weight of with the ASFD method described herein.
Figure 13:
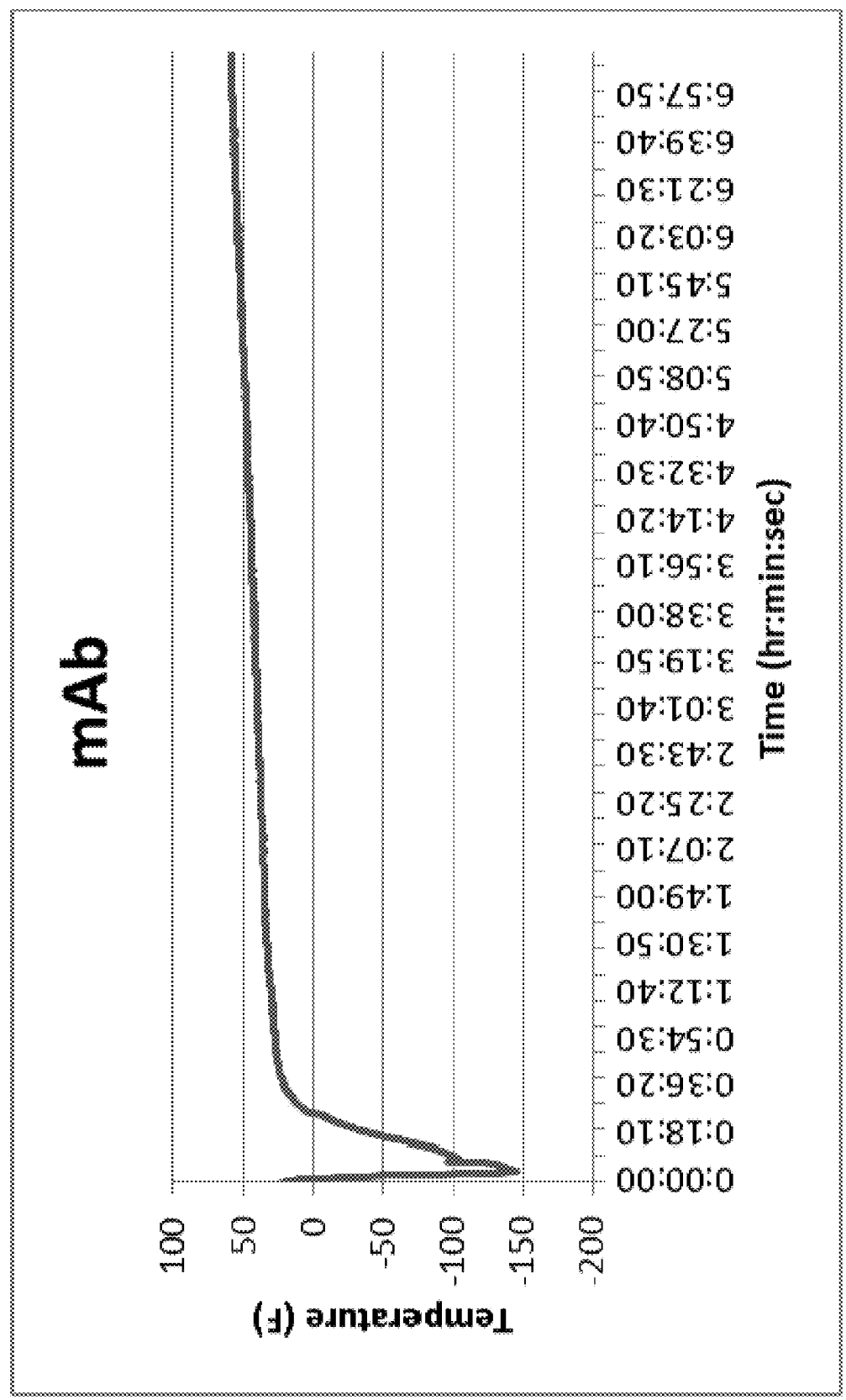
FIG. 13. shows a temperature curve for a monoclonal antibody (mAb) dried from an aqueous solution comprising 12% mAb and 4.6% cryoprotectants by weight of with the ASFD method described herein.
Figure 14:
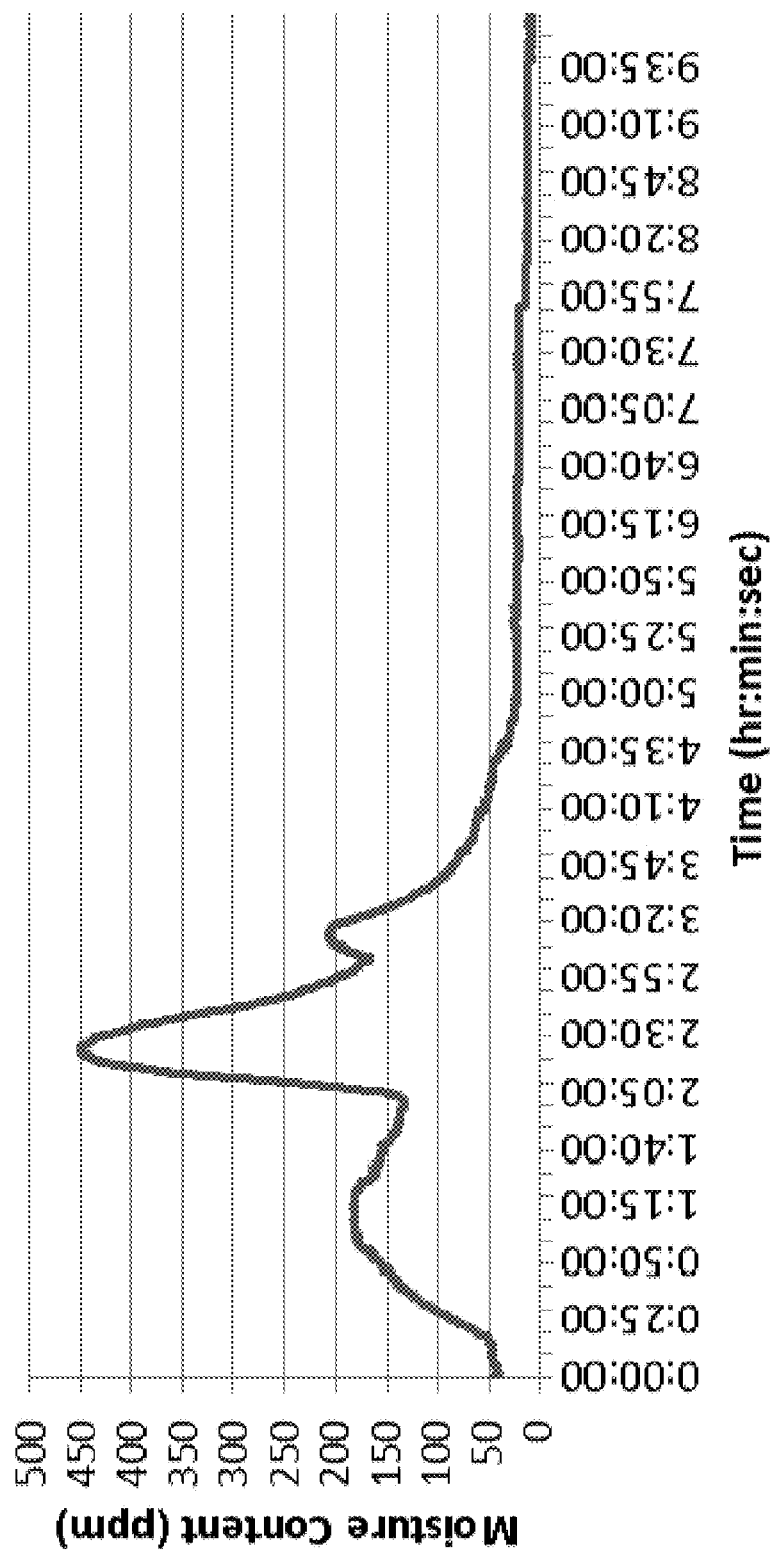
FIG. 14. shows a typical drying curve for Dextran 500 dried from an aqueous 12% solution comprising 0.5% Dextran 500 and 10.5% sucrose by weight of with the ASFD method described herein.
Figure 15:
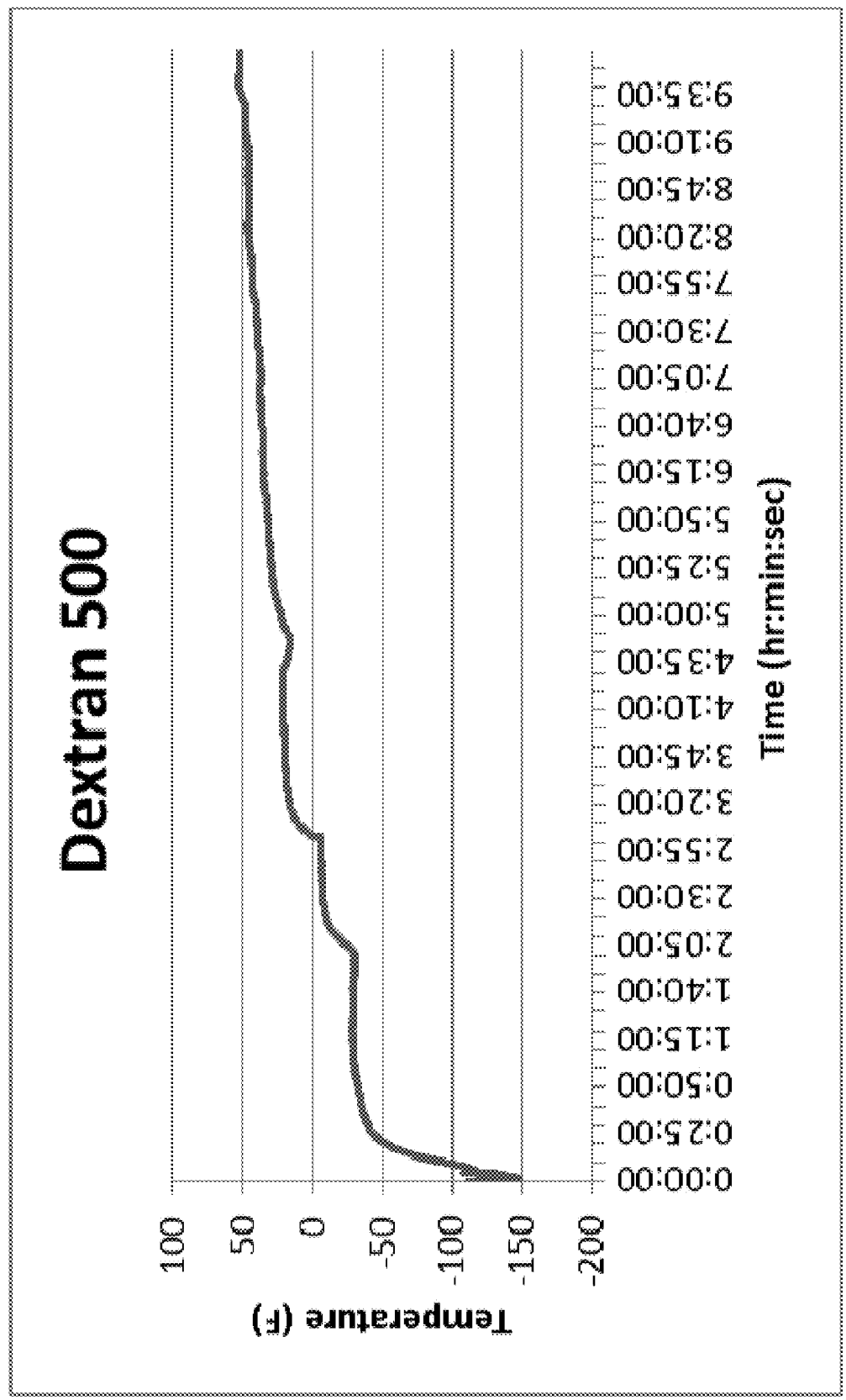
FIG. 15. shows a typical temperature curve for Dextran 500 dried from an aqueous 12% solution comprising 0.5% Dextran 500 and 10.5% sucrose by weight of with the ASFD method described herein.

A typical ASFD run to dry Bovine Gamma Globulin (BGG) was conducted per a stepwise procedure like the following example. A solution of BGG was prepared such that the BGG constituted 10% by weight of an aqueous solution. Once the inner chamber was cooled to a temperature of −140° F., 50 ml of solution was sprayed at a rate of 1 ml per second and at a pressure of 40 psi into the reactor chamber after the flow of cooling gas had been decreased to 5 SCFM. A flow rate of 20 SCFM was then set for drying. Temperature during the first hour was set at 30° F., and increased by five degrees at hour two and hour three. FIG. 10 shows the amount of water in parts per million coming through the filter as measured at the exit hose. FIG. 11 shows the temperature of the drying gas as recorded by the thermocouple nearest the filter. After three hours and thirty minutes the powder was removed from the chamber and tested for water content. Testing showed a moisture content of 4.2%.

Monoclonal Antibody

A typical run to dry a monoclonal antibody (mAb) was conducted per a stepwise procedure like the following example. A solution of a mAb was prepared such that the mAb constituted 12% and cryoprotectants constituted 4.6% by weight of an aqueous solution (All such solutions are formulated for each specific mAb with specific cryoprotectants, each varying from about 1-15% of the dry weight of the solution). Once the inner chamber was cooled to a temperature of −140° F., 25 ml of solution was sprayed at a rate of 1 ml per second and at a pressure of 40 psi into the reactor chamber after the flow of cooling gas had been decreased to 5 SCFM. A flow rate of 20 SCFM was then set for drying. Temperature during the first hour was set at 30° F., and increased by five degrees after each of the next six hours. FIG. 12 shows the amount of water in parts per million coming through the filter as measured at the exit hose. FIG. 13 shows the temperature of the drying gas as recorded by the thermocouple nearest the filter. After seven hours, the powder was removed from the chamber and tested for water content. Testing showed a moisture content of 2.95%.

Dextran 500

A typical run to dry a long chain, complex carbohydrate was conducted per a stepwise procedure like the following example. A solution of a Dextran 500 was prepared such that the Dextran 500 constituted 0.5% and sucrose constituted 10.5% by weight of an aqueous solution. Once the inner chamber was cooled to a temperature of −140° F., 25 ml of solution was sprayed at a rate of 1 ml per second and at a pressure of 40 psi into the reactor chamber after the flow of cooling gas had been decreased to 5 SCFM. A flow rate of 20 SCFM was then set for drying. Temperature was set at −30° F. for the first two hours, increased to −5° F. for one hour, increased to 20° F. for two hours, increased to 30° F. for one hour, and then increased by five degrees F. for the next four hours. FIG. 14 shows the amount of water in parts per million coming through the filter as measured at exit hose. FIG. 15 shows the temperature of the drying gas as recorded by the thermocouple nearest the filter. After ten hours the powder was removed from the chamber and tested for water content. Testing showed a moisture content of 5.16%.

Drying Gas Flow Rate Comparison

In order to test the impact of a lower flow of drying gas compared to a higher flow of drying gas, it was decided to carry out two sets of runs at two different temperatures. Two runs were conducted at 20° F. and two runs were conducted at 30° F. In all runs 50 ml of 10% BSA was sprayed over the period of a minute and frozen in the usual manner at a temperature of −140° F. All runs lasted 3.5 hours. The drying gas flow rate was 20 SCFM for the first hour and then 25 SCFM for the remainder of the run. The drying gas flow rate was 25 SCFM for the full duration of the drying period that followed the spraying.

In the comparison at 20° F., the moisture content of powder from the high flow run was 9.6% and from the low flow run the moisture content was 6.2%. In the comparison at 30° F., the moisture content of powder from the high flow run was 32.6% and from the low flow run the moisture content was 5.5%. Without being bound by a particular theory, it is believed that the higher flow of the drying gas has a packing effect on the powder that creates a resistance to the flow of gas through the powder and that slows the convection drying of the frozen particles. The effect seems to be larger at a higher temperature. The pressure readings in the chamber were consistent with this conclusion. The difference in the pressure readings around the 35-minute mark of the first hour were 1.1 psi at the lower temperature and 5.5 psi at the higher temperature.

Spraying Gas Flow Rate Comparison

In order to test the impact of a lower flow of gas compared to a higher flow of gas at the time of spraying, two runs were compared with each other. During one run the flow of gas was 10 SCFM and during the other run the flow of gas was 5 SCFM. In all other regards the two runs were identical. In both cases 50 ml of 10% BSA was sprayed at a pressure of 40 psi over a one-minute period. In both cases the gas flow during drying was 20 SCFM and the drying time was 3 hours. In both cases the temperature during drying was 30° F. initially and was increased to 35 and then 40° F. after the subsequent two hours.

There was considerable difference in the moisture content of the two samples. The moisture content of the sample sprayed at the higher flow rate was 26.1% as compared to the 1.1% moisture content of the sample sprayed at the lower flow rate. Without being bound by a particular theory, it is believed that the higher flow of the gas during spraying had a packing effect on the powder that creates a resistance to the flow of gas through the powder, thus slowing the convection drying of the frozen particles. The pressure readings in the chamber were consistent with this conclusion. The pressure reading around the 30-minute mark of the first hour was 8.7 psi at the higher flow rate 4.6 psi at the lower flow rate.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of preparing a dried powder of a pharmacologically active composition, comprising the steps of:

a. spraying a carrier liquid into a chamber to form a flow of liquid droplets, wherein the carrier liquid contains a powder-forming ingredient;
b. freezing the liquid droplets into frozen particles;
c. entraining the flow of frozen particles within a net flow of gas, wherein the net flow of gas prevents the frozen particles from accumulating on the walls of the chamber;
d. collecting the frozen particles on a filter;
e. drying the frozen particles by convection; and
f. forming a dry powder.

2. The method of claim 1, wherein the drying of frozen particles by convection is by passing a flow of gas downward through the frozen particles to remove the carrier liquid.

3. The method of claim 1, wherein the liquid droplets are snap frozen at a freezing temperature of not greater than −75° C.

4. The method of claim 1, wherein the gas has an initial temperature range below the freezing temperature of the liquid particles and subsequent temperatures during drying of the frozen particles above the freezing temperature of the liquid particles.

5. The method of claim 1, wherein the method is performed in the presence of vibration, internals, mechanical stirring, and/or agitation.

6. The method of claim 1, wherein the powder-forming ingredient is a pharmaceutically active compound.

7. The method of claim 6, wherein the powder-forming ingredient further comprises one or more selected the group consisting of a bulking agent, a surfactant, a cryoprotectant, a lyoprotectant, an excipient, and a stabilizer.

8. The method of claim 1, wherein e frozen particles will have a median diameter of up to 200 μm.

9. The method of claim 1, wherein the frozen particles will have a median diameter of up to 500 μm.

10. The method of claim 1, wherein the frozen particles will have a median diameter of up to 1000 μm.

11. The method of claim 1, wherein the frozen particles will have a median diameter of up to 1500 μm.

12. The method of claim 1, wherein step d, is carried out outside the chamber.

13. The method of claim 1, wherein step e and step f are carried out outside the chamber.

14. The method of claim 1, wherein the powder-forming ingredient is suspended or dissolved in the carrier liquid at a concentration greater than about 20 wt % prior to spraying the carrier liquid into the chamber.

15. A dried powder of a pharmacologically active composition produced by the method of claim 1, wherein the dried powder of a pharmacologically active composition is a fragile molecule comprising a protein, a hormone, an antibody, a vaccine, or blood plasma.

16. A dried powder of a pharmacologically active composition produced by the method of claim 1, wherein the dried powder of a pharmacologically active composition comprises a bulking agent or a surfactant.

17. A dried powder of a pharmacologically active composition produced by the method of claim 1, wherein the dried powder of a pharmacologically active composition comprises a cryoprotectant or lyoprotectant.

18. A dried powder of a pharmacologically active composition produced by the method of claim 1, wherein the dried powder of a pharmacologically active composition comprises an excipient or a stabilizer.

19. The method of claim 1, wherein the net flow of gas is less than about 8 SCFM in step c.

20. The method of claim 1, wherein the net flow of gas is greater than about 5 SCFM in step c.

21. The method of claim 1, wherein the drying in step e occurs in a net flow of gas of less than about 25 SCFM.

22. The method of claim 1, wherein the drying in step e occurs in a net flow of gas of greater than about 16 SCFM.

* * * * *